(12) United States Patent
Yost et al.

(10) Patent No.: US 10,352,952 B2
(45) Date of Patent: Jul. 16, 2019

(54) AUTOMATED SAMPLING DEVICE

(71) Applicant: Elemental Scientific, Inc., Omaha, NE (US)

(72) Inventors: Tyler Yost, Omaha, NE (US); David Diaz, Bennington, NE (US); Daniel R. Wiederin, Omaha, NE (US); Kevin Hahn, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 0 days.

(21) Appl. No.: 16/125,135

(22) Filed: Sep. 7, 2018

(65) Prior Publication Data
US 2019/0137529 A1 May 9, 2019

Related U.S. Application Data

(63) Continuation of application No. 15/713,054, filed on Sep. 22, 2017, now Pat. No. 10,073,106, which is a continuation of application No. 15/350,779, filed on Nov. 14, 2016, now Pat. No. 9,772,340, which is a continuation of application No. 14/525,531, filed on Oct. 28, 2014, now Pat. No. 9,523,700.

(60) Provisional application No. 61/896,452, filed on Oct. 28, 2013.

(51) Int. Cl.
| | | |
|---|---|---|
| G06K 7/10 | (2006.01) | |
| G06K 7/14 | (2006.01) | |
| G01N 35/00 | (2006.01) | |
| G06K 19/06 | (2006.01) | |
| G01N 35/10 | (2006.01) | |

(52) U.S. Cl.
CPC ... *G01N 35/00732* (2013.01); *G06K 7/10564* (2013.01); *G06K 7/1417* (2013.01); *G06K 19/06037* (2013.01); *G01N 35/1011* (2013.01); *G01N 2035/00752* (2013.01); *G01N 2035/00831* (2013.01); *G01N 2035/00841* (2013.01); *G01N 2035/00851* (2013.01); *G01N 2035/00881* (2013.01)

(58) Field of Classification Search
CPC ................................................. G01N 35/00732
USPC ........................... 235/375; 73/61.55; 422/62
See application file for complete search history.

(56) References Cited

U.S. PATENT DOCUMENTS

| | | |
|---|---|---|
| 2005/0002828 A1 | 1/2005 | Gunji |
| 2005/0013737 A1 | 1/2005 | Chow |
| 2009/0173161 A1 | 7/2009 | Kibblewhite et al. |
| 2009/0176208 A1 | 7/2009 | Brodie |
| 2009/0291449 A1 | 11/2009 | Knapp, Jr. et al. |
| 2010/0215548 A1 | 8/2010 | De Luca et al. |
| 2012/0308435 A1 | 12/2012 | Fritchie |
| 2013/0014566 A1 | 1/2013 | Marks |

(Continued)

*Primary Examiner* — Allyson N Trail
(74) *Attorney, Agent, or Firm* — Kevin West; Advent, LLP

(57) ABSTRACT

A sample identification system for an automated sampling and dispensing device is described. In an example implementation, the sample identification system includes a sample probe configured to contact a sample positioned within a sample vessel. Further, the sample identification system includes an identifier capture device configured to measure a sample identifier associated with the sample vessel and generate a data signal in response thereto, where the data signal corresponds to an identity of the at least one sample. During operation, the identifier capture device scans a sample holder, a sample vessel, or a table top of the automated sampling and dispensing device to measure the sample identifier and to generate the data signal in response thereto.

20 Claims, 30 Drawing Sheets

(56) References Cited

U.S. PATENT DOCUMENTS

2013/0019697 A1    1/2013   Mckeen et al.
2014/0231524 A1    8/2014   Liou

AUTOMATED SAMPLING DEVICE

CROSS-REFERENCE TO RELATED APPLICATIONS

The present application is a continuation under 35 U.S.C. § 120 of U.S. patent application Ser. No. 15/713,054 filed Sep. 22, 2017, and titled "AUTOMATED SAMPLING DEVICE,", which in turn is a continuation under 35 U.S.C. § 120 of U.S. patent application Ser. No. 15/350,779, filed Nov. 14, 2016, and titled "AUTOMATED SAMPLING DEVICE,", which in turn is a continuation under 35 U.S.C. § 120 of U.S. patent application Ser. No. 14/525,531, filed Oct. 28, 2014, and titled "AUTOMATED SAMPLING DEVICE," which in turn claims the benefit under 35 U.S.C. § 119(e) of U.S. Provisional Application Ser. No. 61/896,452, filed Oct. 28, 2013, and titled "AUTOMATED SAMPLING DEVICE." U.S. patent application Ser. Nos. 15/713,054, 15/350,779 and 14/525,531 and U.S. Provisional Application Ser. No. 61/896,452 are herein incorporated by reference in their entireties.

BACKGROUND

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

SUMMARY

A sample identification system for an automated sampling and dispensing device is described. In an example implementation, the sample identification system includes a sample probe configured to contact a sample positioned within a sample vessel. Further, the sample identification system includes an identifier capture device configured to measure a sample identifier associated with the sample vessel and generate a data signal in response thereto, where the data signal corresponds to an identity of the at least one sample. During operation, the identifier capture device scans a sample holder, a sample vessel, or a table top of the automated sampling and dispensing device to measure the sample identifier and to generate the data signal in response thereto.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Figure 1:
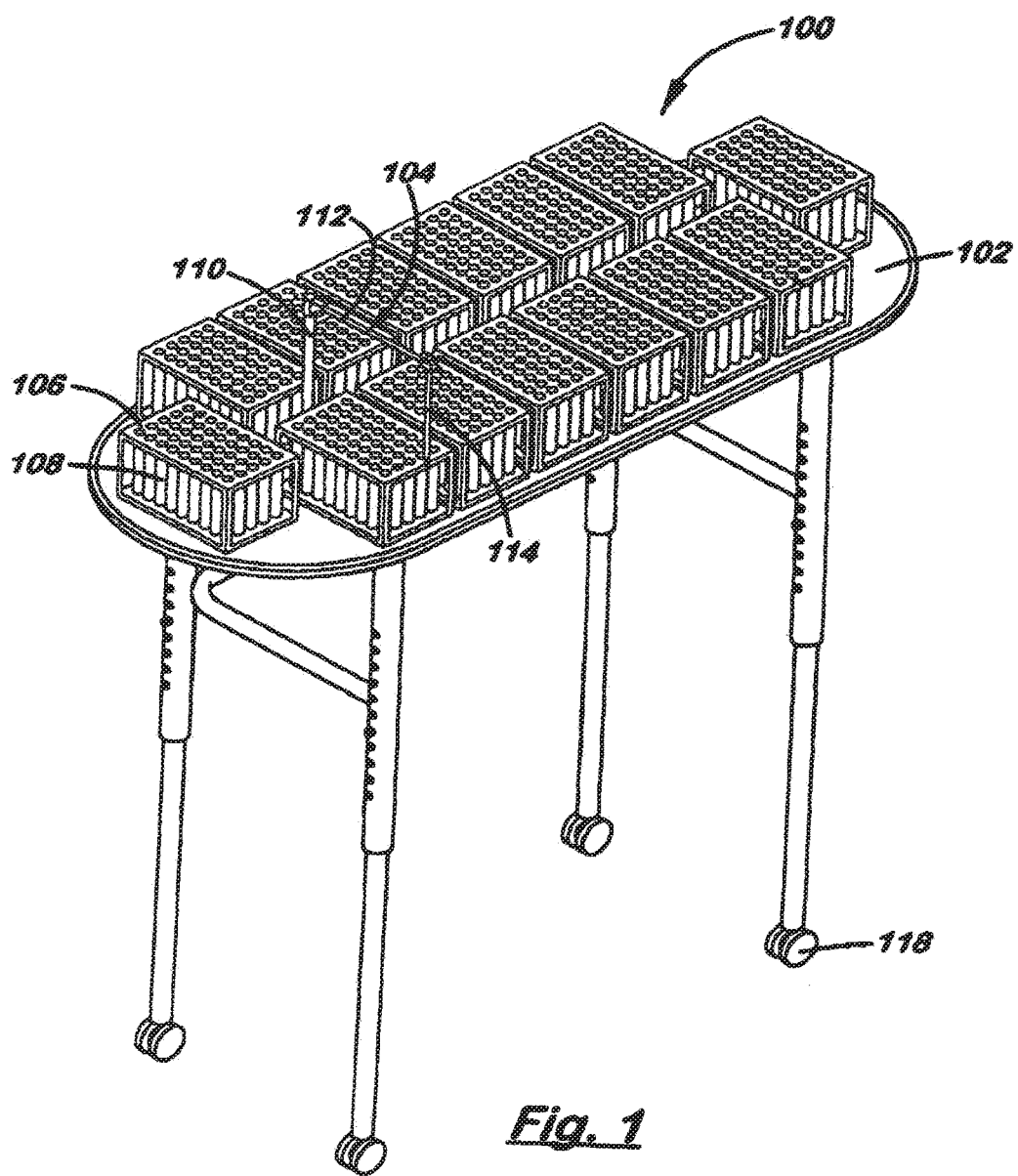
FIG. 1 is an isometric view illustrating an automated sampling or dispensing device in accordance with example implementations of the present disclosure.

FIG. 1 illustrates automated sampling device 100 in accordance with an example implementation of the present disclosure. Automated sampling device 100 includes table top 102 and sample arm assembly 104. Further, sample holders 106 holding multiple sample vessels 108 are present on table top 102 in preparation for sample assaying. It should be understood that automated sampling device 100 may assay from one to many hundreds of samples (e.g., greater than 1200 samples in the example implementation illustrated) in a given time depending upon test requirements. Verification of a sample identify of a sample to be analyzed is described with reference to FIGS. 20 through 26B.

In the implementation illustrated, sample arm assembly 104 includes a z-axis support 110 and a sample probe support arm 112 that supports a sample probe 114. As illustrated, the z-axis is aligned with gravity or a vertical axis. In use, sample probe 114 is mounted to sample probe support arm 112, which is moved through space in three dimensions, or about an axis having y-motion that is a substantially rotary motion and along an axis having x-motion which is at least substantially horizontal linear motion or translation, and along a z-axis that is at least substantially vertical, for linear motion or translation. In an implementation, the length of a sample probe support arm (the length of an arm extending from the y-rotary axis) is no more than one-half the length of a linear translation of the center slot (i.e., is no more than half of the length of x-axis linear motion). In an implementation, the length of the sample probe support arm is approximately equal to one-half the length of a linear translation of the center slot. Such configuration allows nearly one hundred percent of the footprint of the table to be accessed by the sample probe. Footprint is defined as being substantially equivalent to an area encompassed by the area of the table top. In an additional implementation, the y-rotary axis of an automated sampling device allows for access to sample vessels on either side of the x-axis motion of linear travel (i.e., on either side of the center slot).

In an implementation, the components of sample arm assembly 104 are formed of carbon composite materials. Further, all exposed surfaces of the sample arm assembly 104 are made from inert or fluoropolymer-covered materials (i.e., Teflon®). It should be understood, however, that the sample arm assembly may be made with various materials, including aluminum, steel, plastic, and so forth.

In addition, sample arm assembly 104 is designed to attach to various surface supports including a table top. Such assembly may be attached to either side of the center slot. In an implementation, table top 102 may be mounted onto legs with casters 118, rollers and so forth. Such configuration increases the mobility of the automated sampling device, thereby facilitating preparation of samples at a location separate from the analytical instruments. Further, this configuration provides storage room underneath the table top which may be absent with bench-top automated sampling devices. The height of the table is adjustable to compensate for the effects of gravity on liquid flow rates when self-aspirating sampling devices are used. The ability to adjust table top height also allows the automated sampling device to accommodate various sized sample vessels.

Figure 2A:
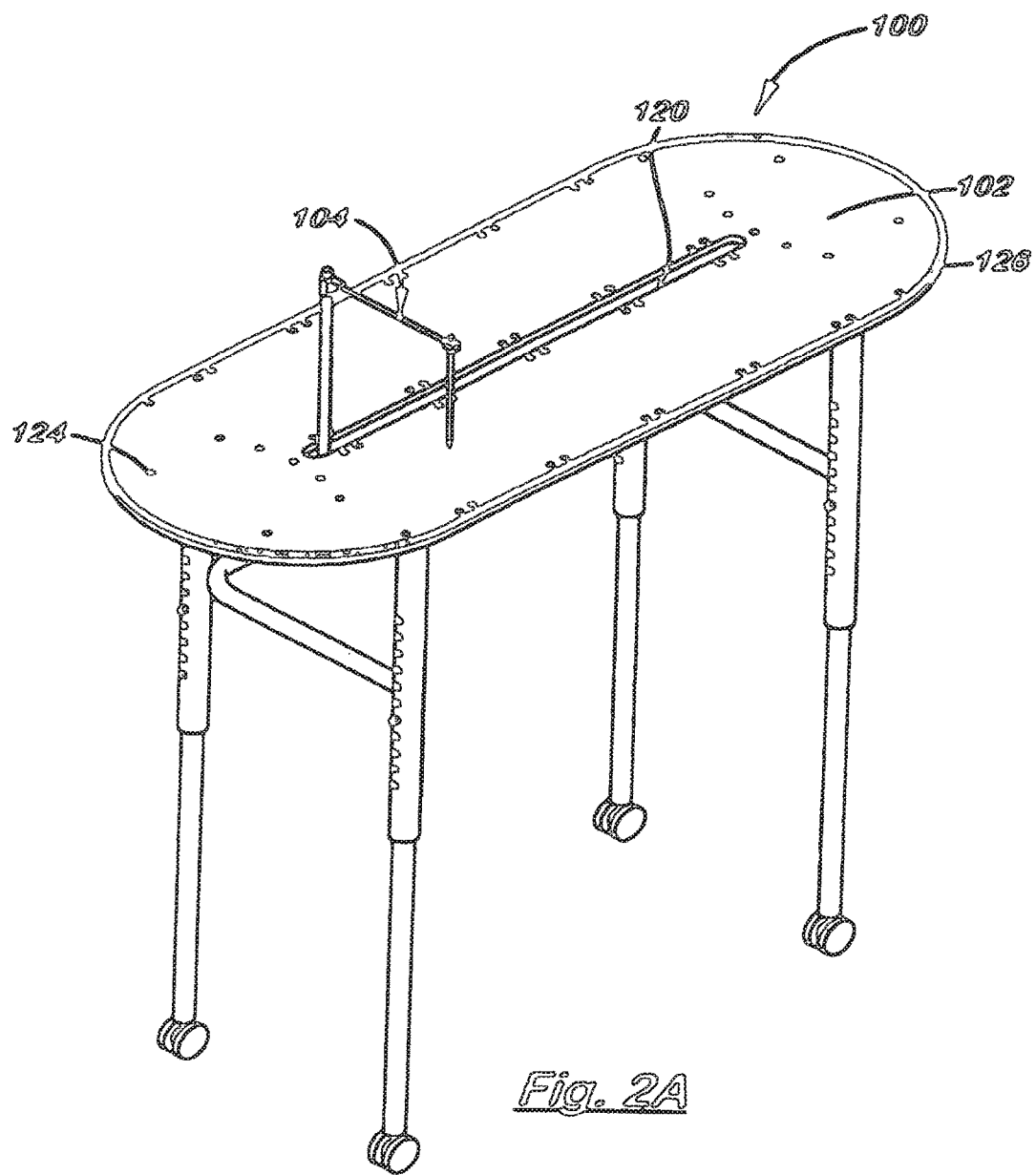
FIG. 2A is a partial isometric view illustrating an automated sampling or dispensing device in accordance with example implementations of the present disclosure, where a center slot in the support surface is present allowing the sample arm assembly to be connected with the drive assembly.
Figure 2B:
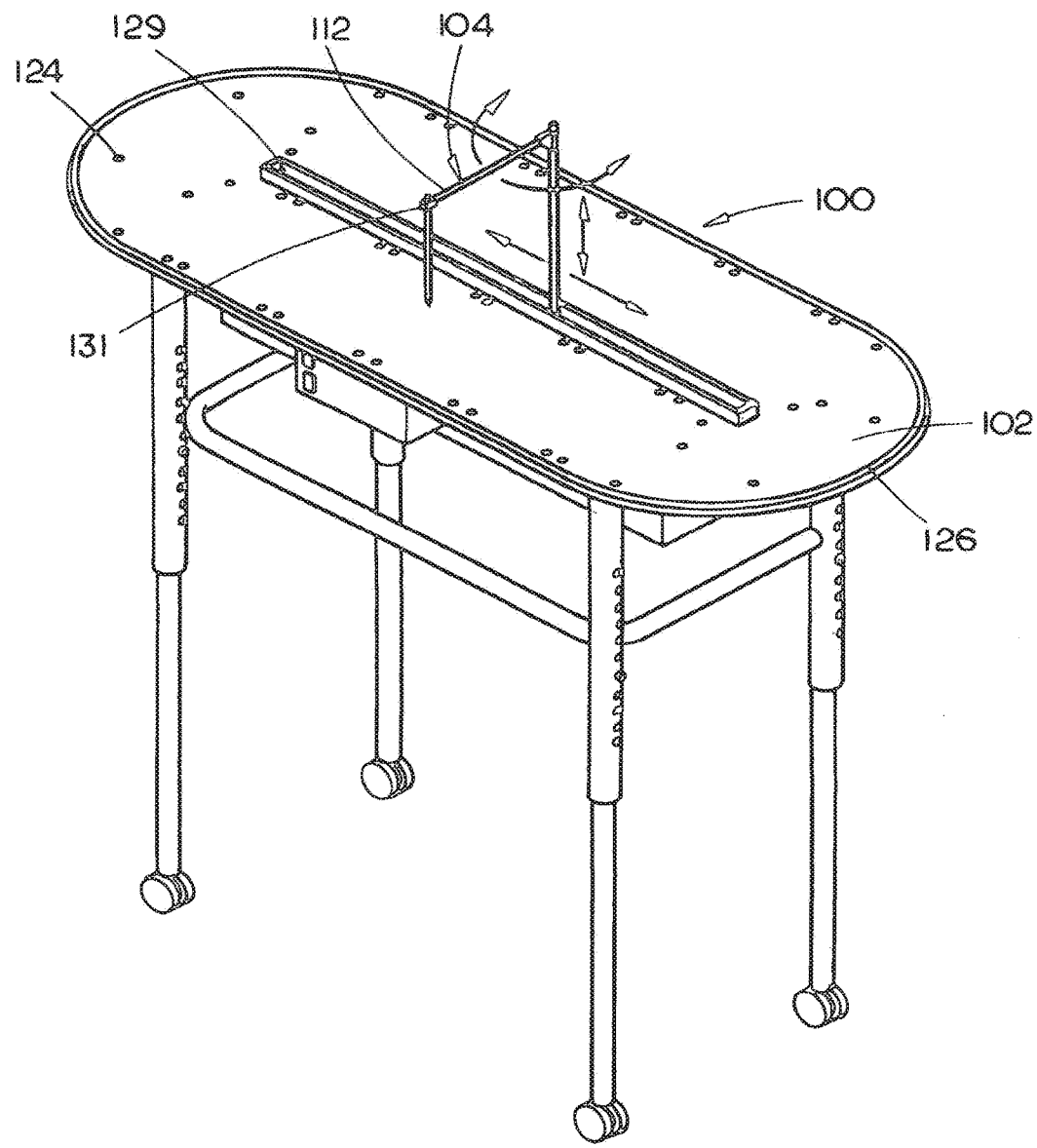
FIG. 2B is a partial isometric view illustrating an automated sampling or dispensing device in accordance with example implementations of the present disclosure, where a raised slot on the support surface is present to attach the sample arm assembly to the drive assembly.

FIGS. 2A and 2B are additional illustrations of automated sampling or dispensing devices in which the sample arm assembly is attached to the drive assembly via a center slot or a raised slot, respectively. In FIG. 2A, automated sampling device 100 is comprised of sample arm assembly 104 extending through center slot 120 and table top 102 including a plurality of recesses 124 and the channel 126. The sample arm assembly 104 is attached to the drive assembly (not shown) via center slot 120. In an implementation, the plurality of recesses is coupled with sensors for detecting the location of sample holders. The sample holder location information may then be transferred to a controller of a drive assembly controlling the sample arm assembly providing the alignment system. The previous configuration allows the sample arm assembly to detect the location of sample vessels on the table top at a given time. Channel 126 runs along the edge of table top 102 to collect possible sample spillage.

In addition to FIG. 2A, FIG. 2B demonstrates an automated sampling or dispensing device including a sample arm assembly 104 attached to the drive assembly 128 via a raised slot 129. In one implementation, a magnet 131 is attached to the end of the sample probe support arm 112 which allows detection of a three-dimensional position in space where the magnet 131 is embedded into the sample probe support arm 112 and is detected by a sensing means such as a Hall Effect sensor.

Figure 3:
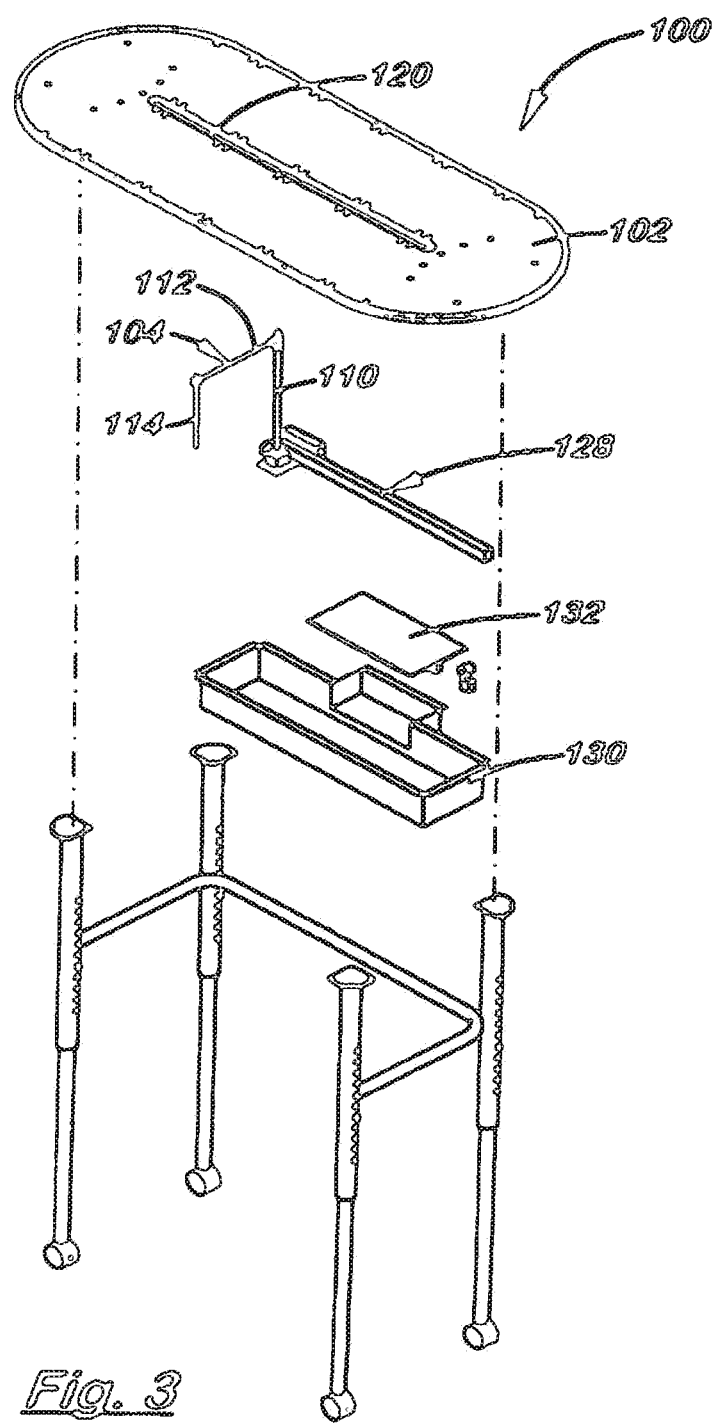
FIG. 3 is an exploded view of the automated sampling or dispensing device shown in FIG. 1, further illustrating components of the device.

Referring now to FIG. 3, an exploded view of the components comprising the automated sampling device 100 is provided. The automated sampling device 100 is comprised of a table top 102 with center slot 120, drive assembly 128, sample arm assembly 104, housing 130, and controller 132. Sample arm assembly 104 includes z-axis support 110 attached to drive assembly 128, sample probe support arm 112 attached to z-axis support 110, and sample probe 114 attached to sample probe support arm 112. Sample arm assembly 104 is controlled by drive assembly 128 and controller 132. In an implementation, drive assembly 128 causes sample arm assembly 104 to move along center slot 120, in translation along an axis coaxial to z-axis support 110, and radially about the z-axis for inserting sample probe 114 into a sample vessel. Further, sample arm assembly 104 is no more than one-half the length of a linear translation of the length of center slot 120. As previously mentioned, such configuration allows nearly one hundred percent of the footprint to be accessed by sample probe 114. In addition, automated sampling device 100 is capable of assaying hundreds of samples at a given time without operator assistance, thereby allowing the operator to perform other tasks. Moreover, it is possible to configure the automated sampling device to assay samples overnight, allowing work productivity to be increased.

To accommodate gross differences in sample vessel height, sample probe support arm 112 may be moved up or down z-axis support 110 as desired prior to sample assaying. Once the desired position is reached, sample probe support arm 112 is secured into a fixed position on z-axis support 110 and sample vessels containing samples may be loaded onto the table top. This feature allows the automated sampling device to be used on various sizes of sample vessels while still not having mechanical moving parts above stationary samples. Additionally, housing 130 encloses drive assembly 128 to protect the assembly from debris, dust, contaminates, and so forth. Housing 130 may be made of various materials, e.g., blow molded polyethylene, and so forth.

Figure 4A:
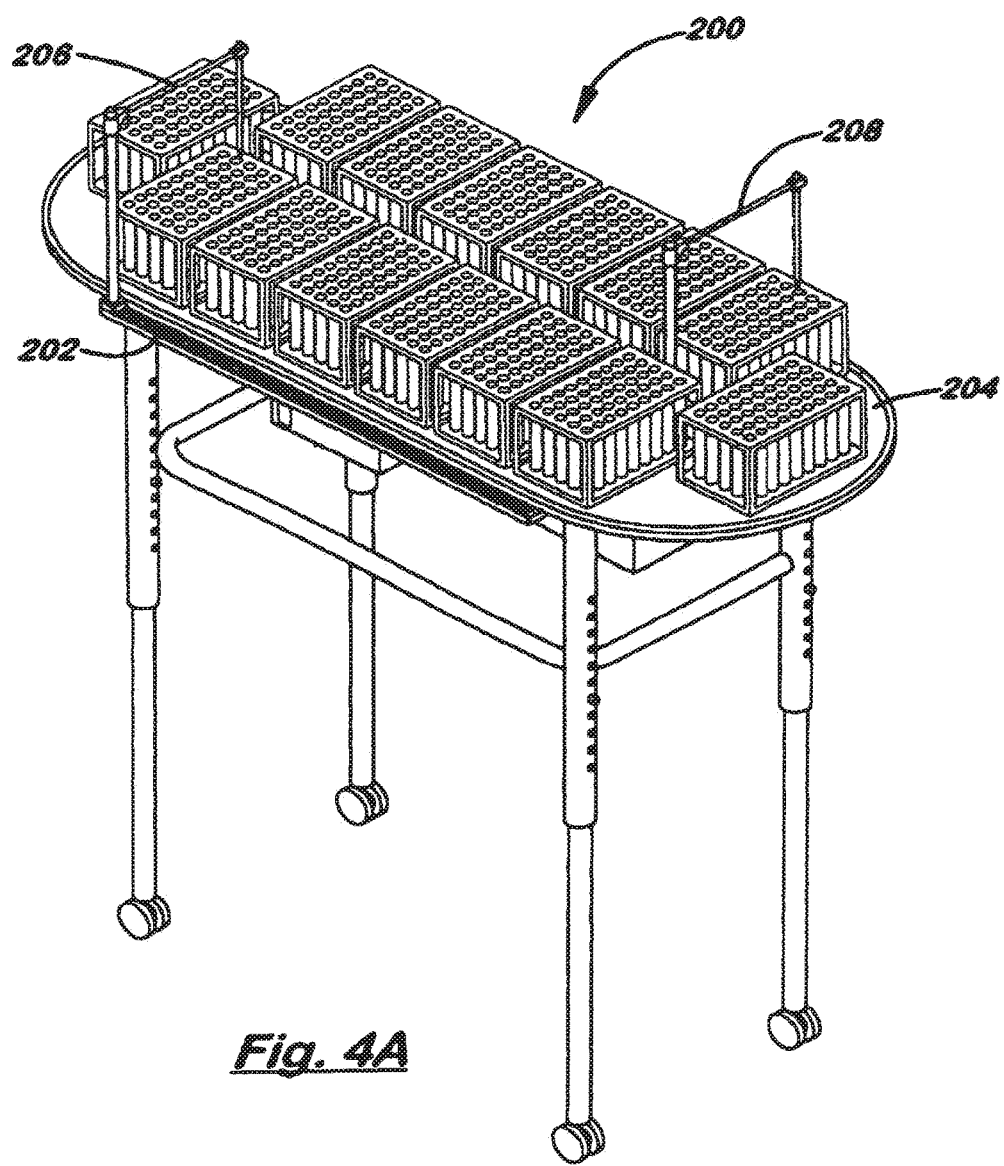
FIG. 4A is an isometric view illustrating an automated sampling or dispensing device in accordance with example implementations of the present disclosure where multiple sampling arm assemblies and drive assemblies are mounted to the top of the support surface of the automated sampling or dispensing device.
Figure 4B:
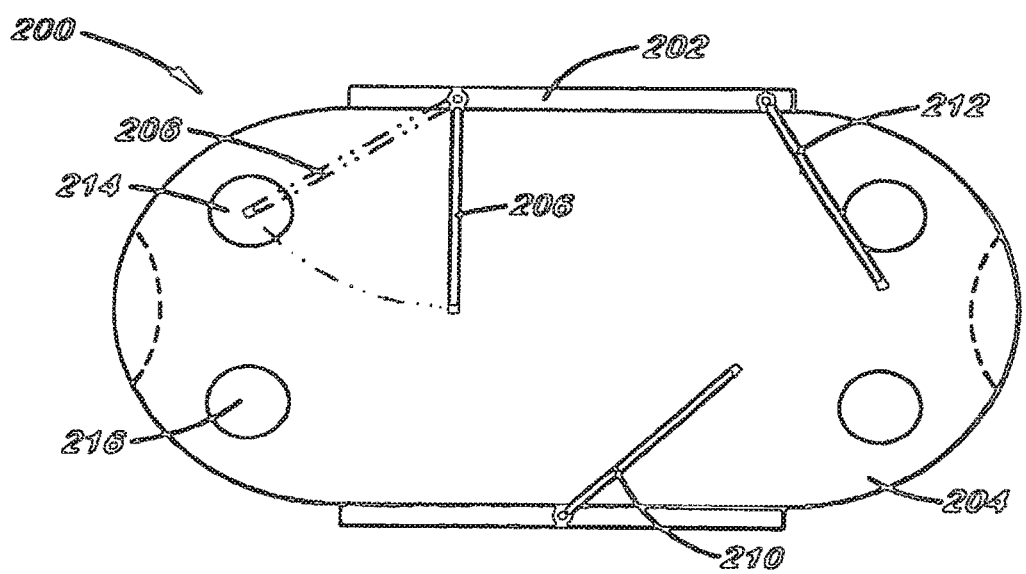
FIG. 4B is a plan view illustrating an automated sampling or dispensing device in accordance with example implementations of the present disclosure, where multiple sample arm assemblies and rinse stations are present on one support surface.

FIGS. 4A and 4B illustrate an automated sampling device 200 in accordance with another example implementation of the present disclosure, where multiple sampling arm assemblies (i.e., sample arm assembly 206, 208, and 210) are mounted to the table top of the automated sampling device. Automated sampling device 200 includes multiple automated sampling devices attached to a table top at one time. A rail 202 is attached to the edge of table top 204 to enable the attachment of additional sample arm assemblies (i.e., sample arm assembly 206 and 212). Utilization of additional sample arm assemblies allows multiple sample zones to be configured (i.e., a prep zone, an assaying zone, and so forth).

In additional implementations, various types of multiple rinse or eluent stations may be included in the automated sampling device. For instance, multiple rinse stations (i.e., 214 and 216) of the overflow type designed to reduce the chance of carry-over contamination may be present. Further, overflow rinse stations may contain a series of different chemical rinses to reduce contamination between sample analyses (e.g., surfactant, nitric acid, hydrofluoric acid, and/or deionized water). For multiple eluent stations, the automated sampling device may contain such stations for step elution from a chromatographic column.

Figure 5:
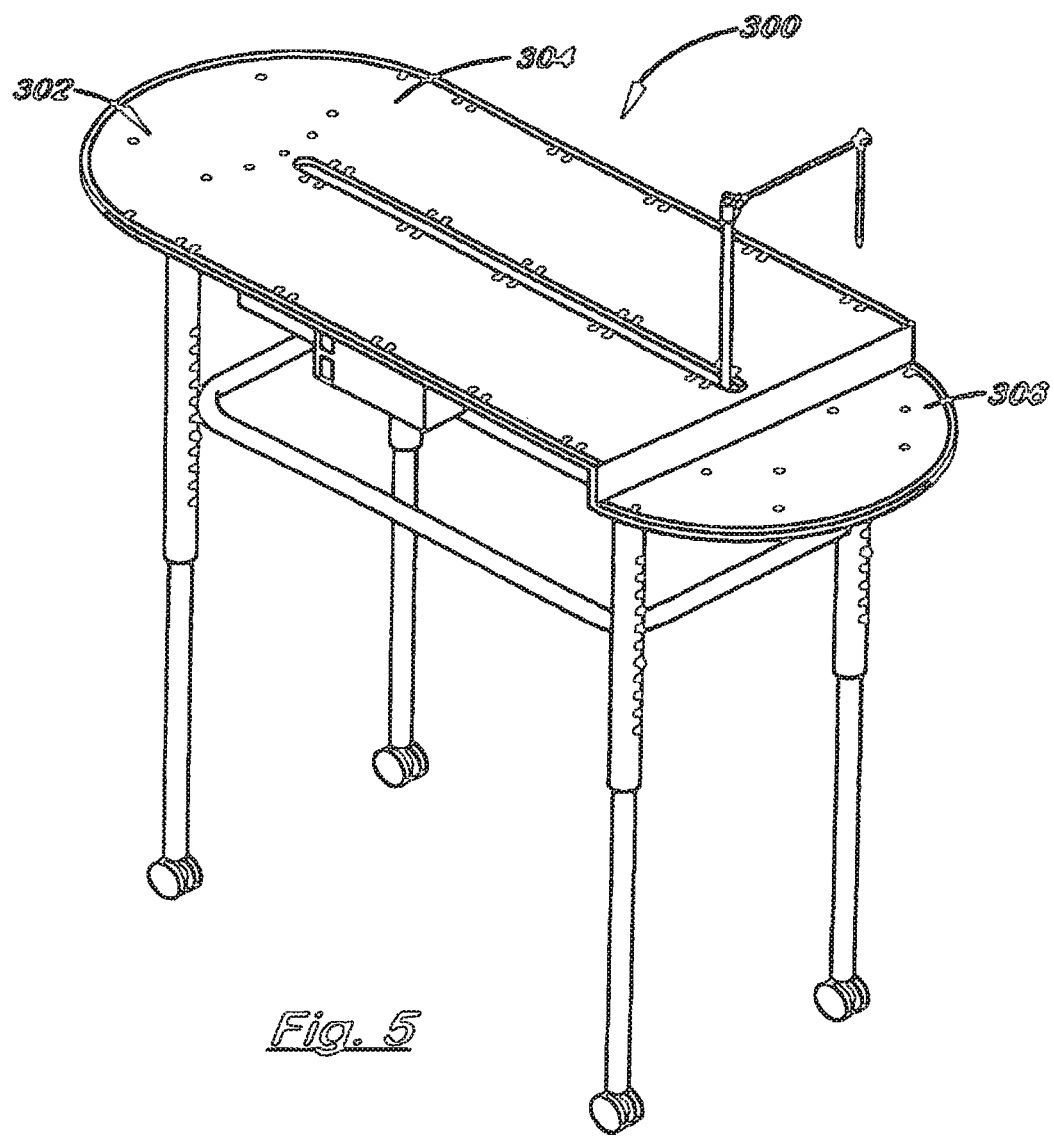
FIG. 5 is an isometric view illustrating an automated sampling or dispensing device in accordance with example implementations of the present disclosure, where the support surface of the automatic sampling or dispensing device is provided with more than one plane.

Referring now to FIG. 5, an automated sampling device in accordance with another example implementation of the present disclosure is described, where a table top having more than one plane is provided. Automated sampling device 300 includes table top 302 which has more than one plane, plane one 304 and plane two 306. Such configuration allows table top 302 to accommodate various sizes of vessels. For instance, the height of vessels in plane two 306 may be taller than vessels in plane one 304 of table top 302.

Figure 6:
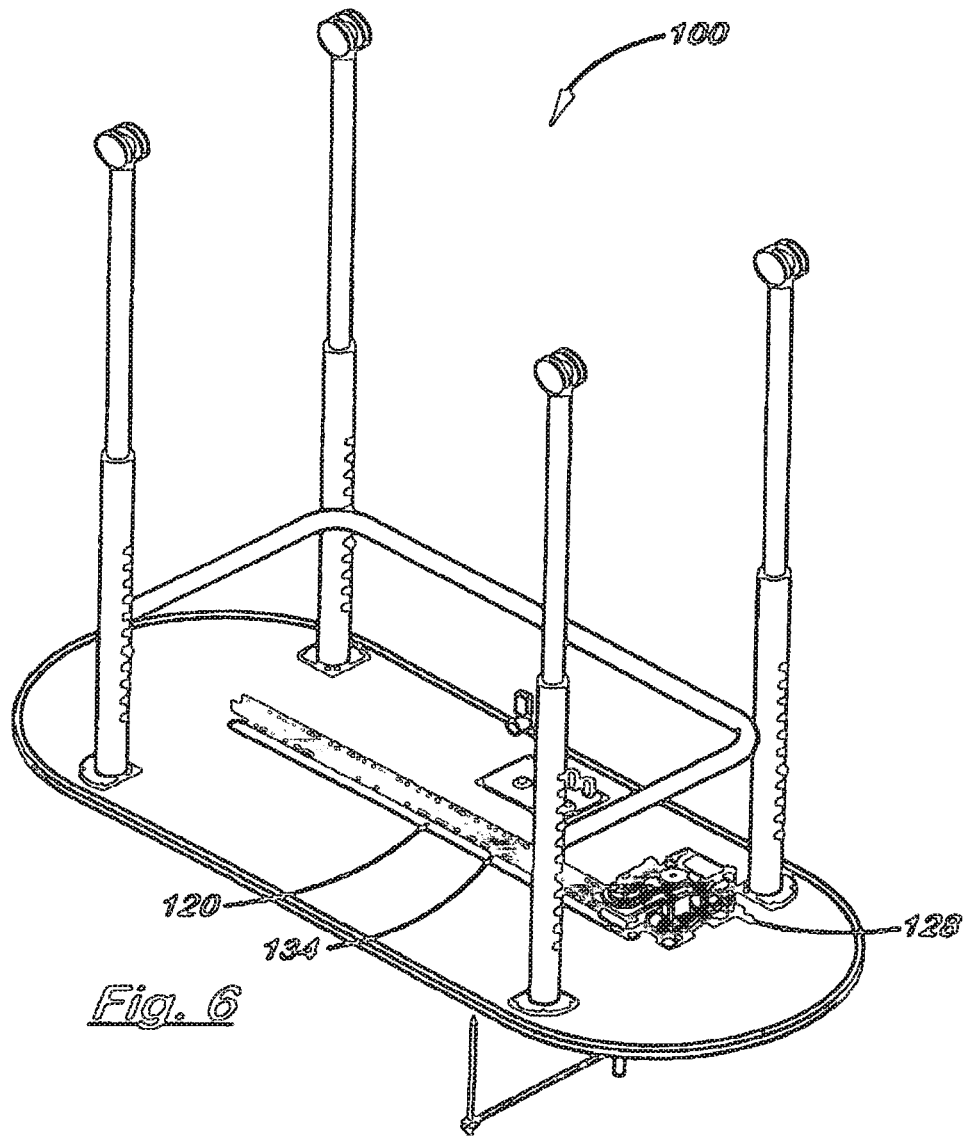
FIG. 6 is an isometric view of the automated sampling or dispensing device shown in FIG. 1, further illustrating the drive assembly.
Figure 7:
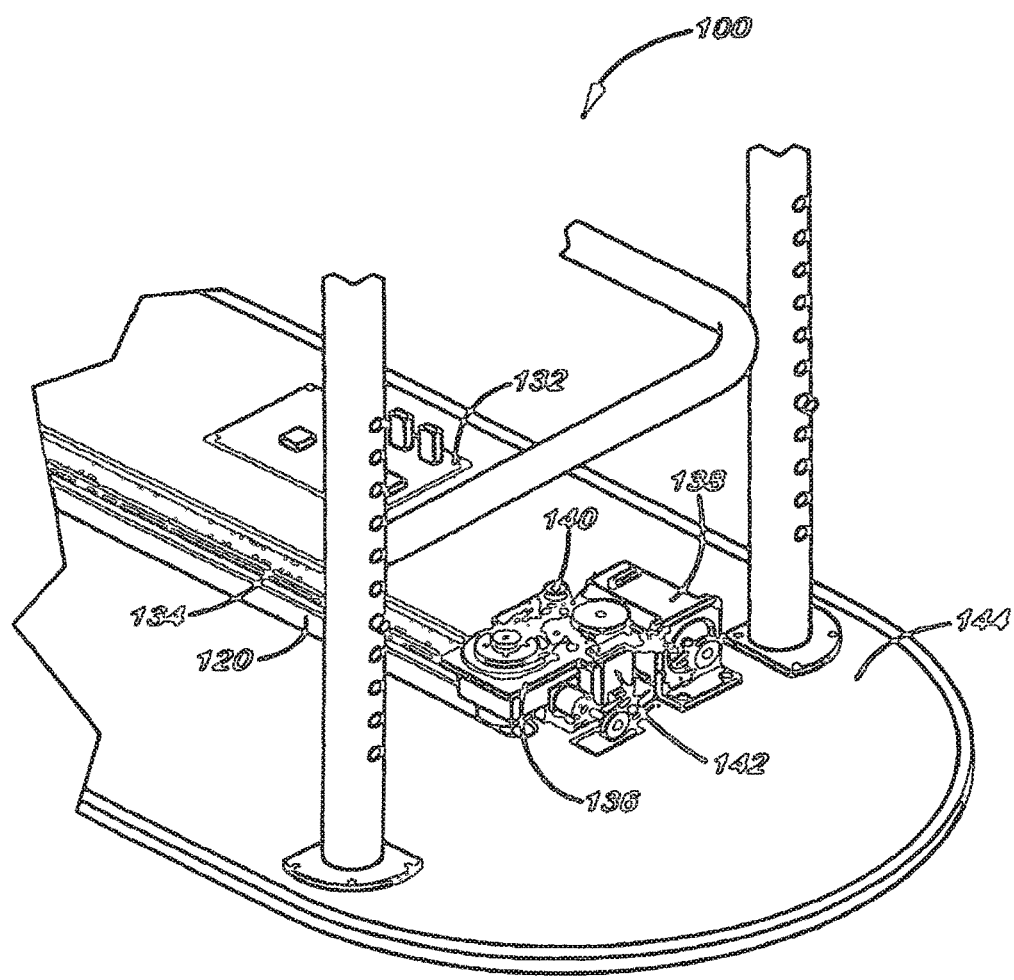
FIG. 7 is a partial isometric view of the drive assembly shown in FIG. 6, further illustrating components of the drive assembly.

FIGS. 6 and 7 further illustrate a drive assembly of automated sampling device 100 attached to a table top bottom. FIG. 6 provides an overview of a drive assembly in accordance with the present disclosure, depicting a linear drive 134 running parallel to center slot 120 and connected to sled 128. FIG. 7 is an enlarged view of the drive assembly illustrated in FIG. 6. Drive assembly 100 is comprised of motor one 138, motor two 140, motor three 142, sled 136, linear drive 134, and controller 132. Motor one 138 controls translation of a sample arm assembly's movements along the center slot 120 and is attached to table top bottom 144 and linear drive 134. Various stepper motors may be used to control translation of the sample arm assembly's movements along center slot 120. Moreover, it will be appreciated that various linear drives may be used including a worm drive. Motor two 140 controls angular rotation of a sample arm assembly and is connected to sled 136. In an implementation, motor two 140 is a radial motor. Motor three 142 controls vertical movement of a sample arm assembly and is attached to sled 136. Various stepper motors may be used for controlling vertical movement of the sample arm assembly. In an additional implementation, motor three 142 comprises a slip-clutch system. Further, in accordance with the present disclosure, the drive assembly may be hard-wired or, in another implementation, controlled via wireless communication. Thus, wireless communications may be used to connect controller 132 with the desired analytical instrument (not shown). Utilization of wireless communications allows sample assaying to occur without requiring physical connection with a controller computer increasing mobility of the automated sampling device.

Figure 8:
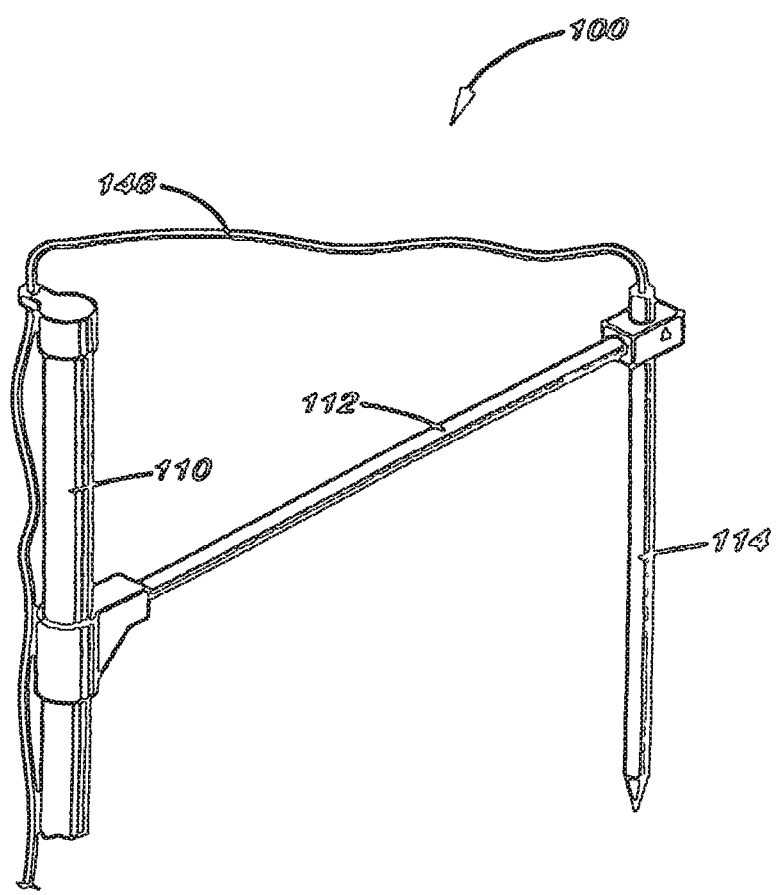
FIG. 8 is a partial isometric view illustrating a sample arm assembly for an automated sampling or dispensing device in accordance with example implementations of the present disclosure.

FIG. 8 provides a detailed depiction of a sample arm assembly of an automated sampling device in accordance with the first example implementation of the present disclosure. As previously described, the sample arm assembly includes z-axis support 110 attached to a drive assembly (see FIGS. 6 and 7), sample probe support arm 112 attached to z-axis support 110, and sample probe 114 attached to sample probe support arm 112. In an implementation, the sample arm assembly is attached to the drive assembly via the z-axis support extending through a center slot in the table top; in such implementation, the drive assembly is attached to a table top bottom. However, it should be understood that the drive assembly may be disposed in a variety of locations including on top of the table top without departing from the scope of the present disclosure.

In an additional implementation in accordance with the present disclosure, sample tubing 146 is present to allow sample removal or reagent delivery as desired. Further, a slip bearing is built into sample probe 114 to prevent winding of sample tubing 146. It is contemplated that the sample may be delivered to various types of scientific instrumentation (e.g., an inductively couple plasma system, a mass spectrometer, and so forth) or a number of other types of vessels (e.g., a waste collecting bucket following a wash step). It is further contemplated that the sample tubing may be flexible (as shown) or rigid, e.g., comprised of plastic, metal, and so forth. In another implementation, the automated sampling device may be equipped with one or more independent components for the purpose of sample preparation, sample dilution, addition of standards to samples or sample acidification.

Figure 9A:
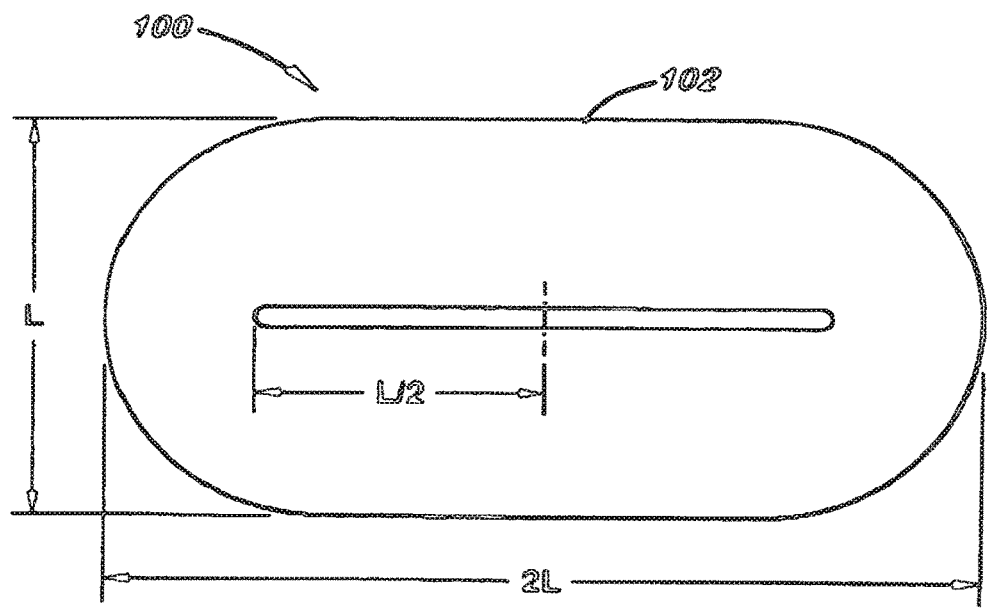
FIG. 9A is a plan view illustrating a support surface for use with an automated sampling or dispensing device, where the support surface includes a slot and has a footprint in accordance with example implementations of the present disclosure.
Figure 9B:
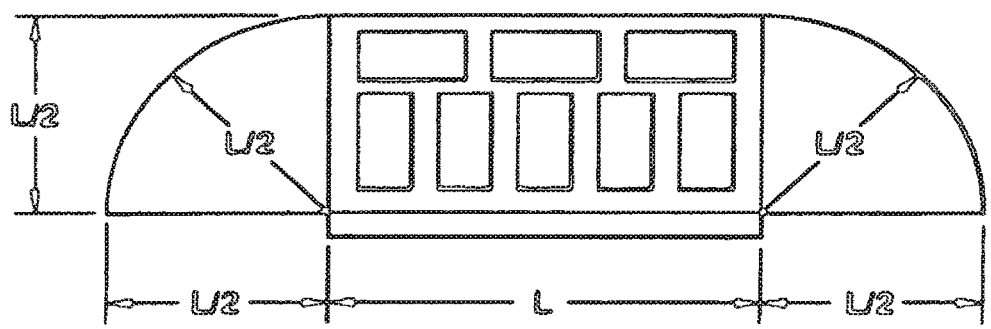
FIG. 9B is a plan view illustrating a support surface for use with an automated sampling or dispensing device, in accordance with example implementations of the present disclosure.

Referring to FIGS. 9A and 9B, tables for use with an automated sampling device are described in accordance with example implementations of the present disclosure. First, the table 102 includes a slot of length L providing for translation of the sample arm assembly along the length of the table. Further, the table 102 has a footprint for maximizing the usable area of the table 102. As illustrated in FIG. 9A, the table 102 has a width L substantially equal to the length of the slot L. Moreover, the table 102 is twice as long as the slot, having a length of 2L. Further, the arm length of a sample probe assembly (as shown in FIGS. 1, 2, and 3) is half the length of the slot, having length L/2. This configuration allows for approximately one hundred percent of the footprint of the table to be accessed. In contrast, FIG. 9B illustrates an additional implementation in accordance with the present disclosure whereby the table is the shape of a semi-circle and a non-centered slot system is employed.

Figure 10:
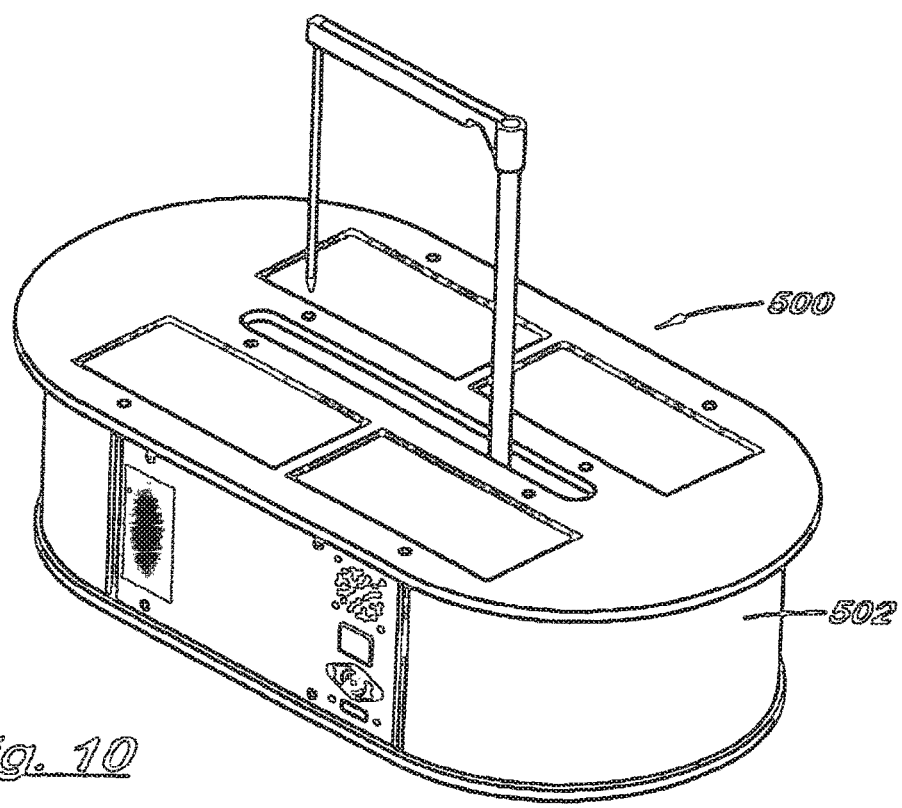
FIG. 10 is an isometric view illustrating an automated sampling or dispensing device in accordance with example implementations of the present disclosure, where the device includes a shroud.

Referring to FIG. 10, automated sampling or dispensing device 500 includes a shroud 502. In an example implementation, the shroud 502 substantially encloses the drive assembly 128 (FIG. 3) for protecting the drive assembly from dust and debris, and/or preventing dust and debris from the drive assembly from contaminating samples during assaying.

Figure 11:
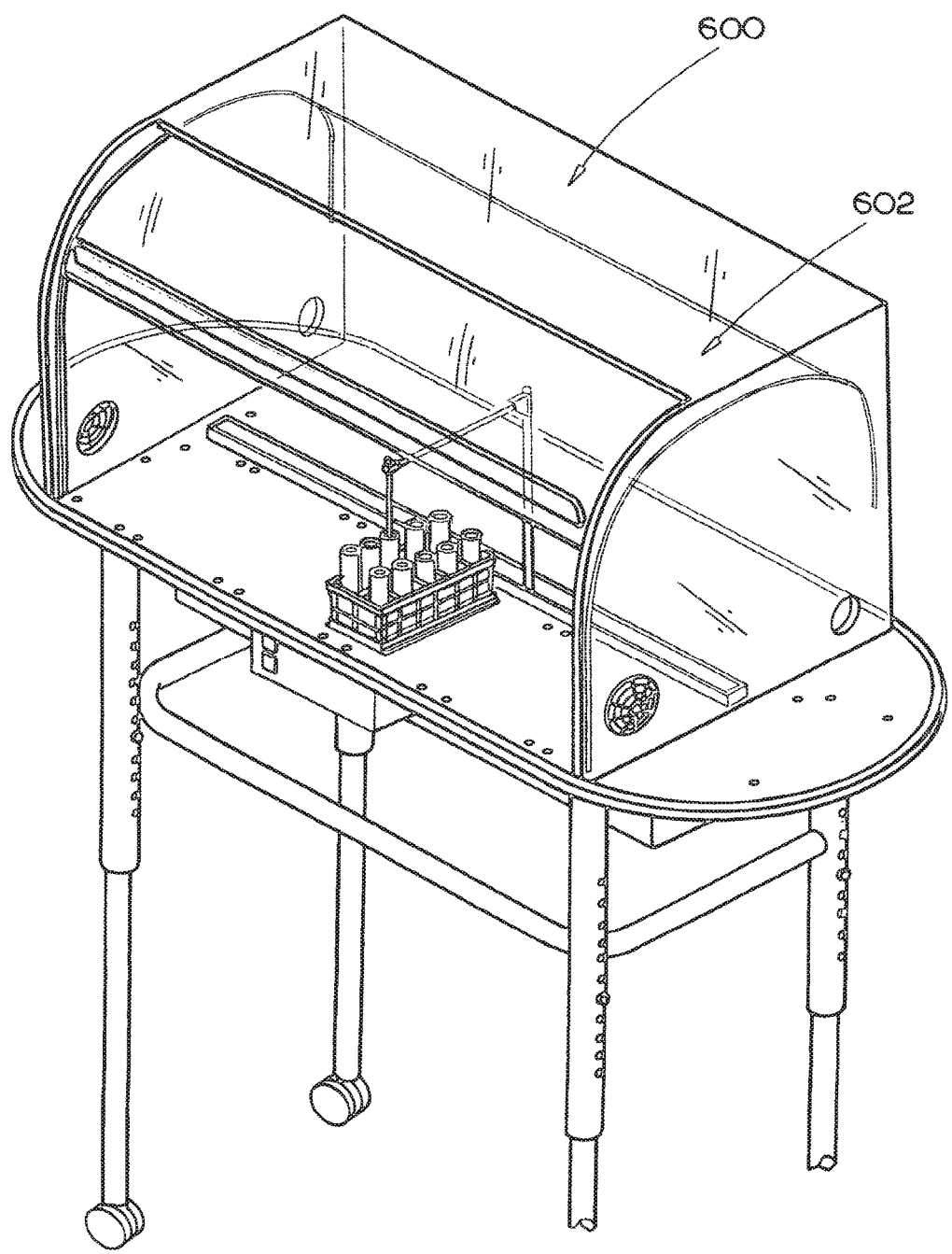
FIG. 11 is an isometric view illustrating an automated sampling or dispensing device in accordance with example implementations of the present disclosure, where the device is contained within a hood.

FIG. 11 illustrates automated sampling device 600 completely enclosed within a hood 602. Use of the hood allows the operations inside the hood to be isolated from the outside environment. The area within the hood may be ventilated to prevent the entry of contaminates such as bacteria or airborne substances. In one specific implementation, the air drawn into the enclosure is passed through a high efficiency particulate air (HEPA) filter. Further, processing of samples which contain hazardous chemicals within a hood allows such samples to be processed without further exposing the user to such chemicals during processing.

Referring generally to FIGS. 12 through 19, various implementations of an enclosure for an automated sampling/dispensing device are provided. In general, the enclosure includes at least one support member. The support member is generally perpendicular to a support surface on which the automated sampling/dispensing device is mounted. Further, a lid is mechanically coupled to the at least one support member for covering the support surface on which the automated sampling/dispensing device is mounted. Additionally, at least one flexible sheet is operationally coupled to at least one of the lid or the at least one support member. The at least one support member may provide support to both the lid as well as the at least one flexible sheet. The at least one support member, lid, and at least one flexible sheet enclose the automated sampling device while allowing access to the device by retracting the at least one flexible sheet.

The presently described example enclosures may minimize user exposure to the enclosed samples by allowing the containment of potentially hazardous chemicals within such enclosure. Further, the use of at least one flexible panel allows the enclosure to be shipped efficiently, as the enclosure may be disassembled into smaller pieces and thus be shipped in a smaller box when compared to enclosures with non-flexible panels/doors. Moreover, the use of the at least one flexible panel allows the enclosure to be shaped to accommodate varying shaped automated sampling and or dispensing devices and assemblies.

Figure 12:
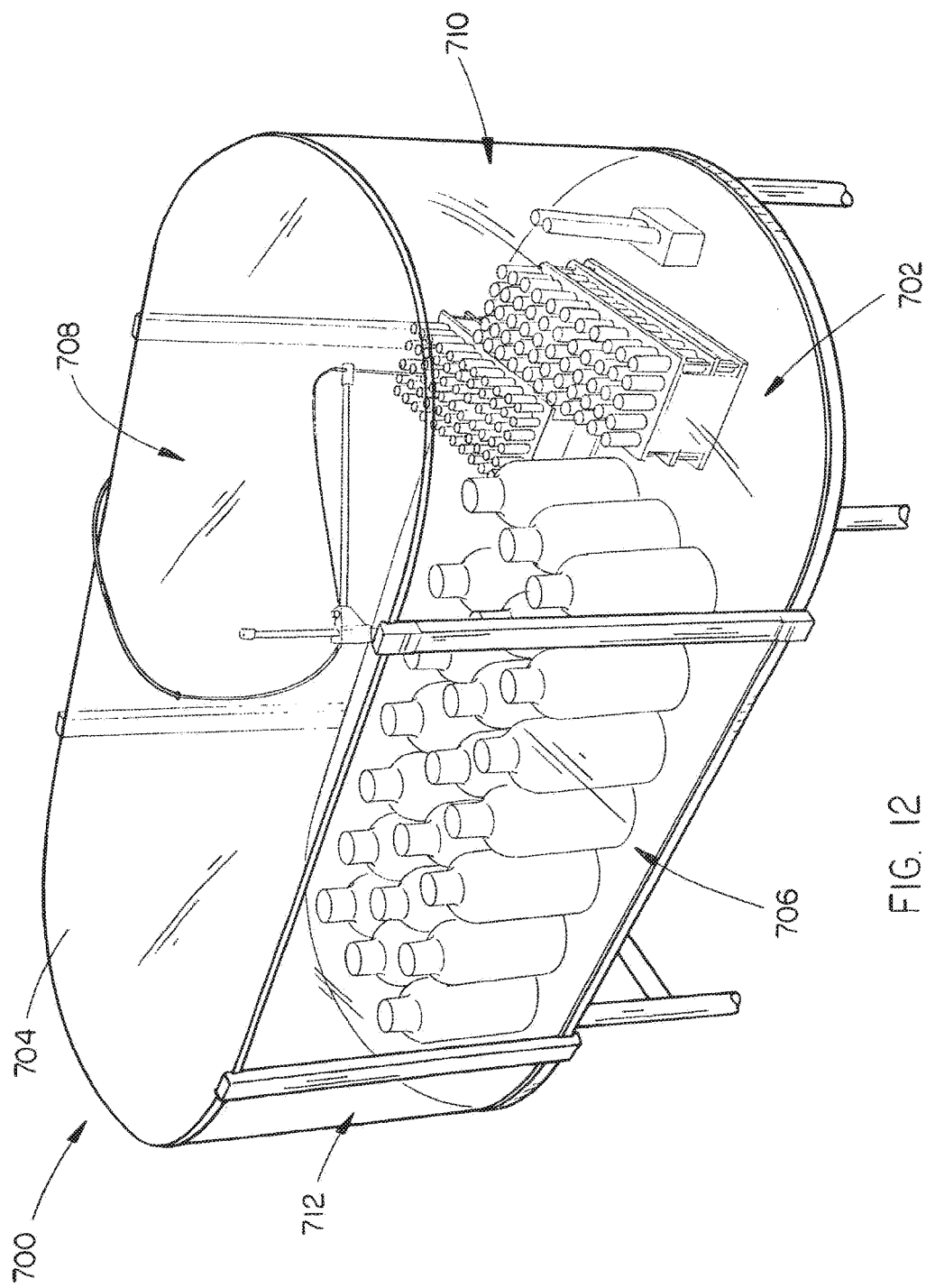
FIG. 12 is an isometric view illustrating an automated sampling or dispensing enclosure in accordance with example implementations of the present disclosure, where the enclosure includes two flexible sheets.

Referring to FIG. 12, an enclosure 700 for an automated sampling/dispensing device is provided in which the enclosure 700 surrounds an automated sampling/dispensing device mounted to a circular support surface 702. In an example implementation, the enclosure 700 includes a lid 704 for covering the support surface 702 on which the automated sampling/dispensing device is mounted. In such implementation, the lid 704 is generally equivalent in shape and size to that of the support surface 702 allowing the entire support surface 702 to be enclosed and available for use by a user. Further, an aperture for allowing the automated sampling/dispensing device to be connected with devices external to the enclosure may be defined within the lid. As illustrated in FIG. 12, an aperture defined within the lid 704 of the enclosure 700 allows a supply tube to the automated sampling/dispensing device to be connected with external laboratory analysis equipment. In another implementation, the enclosure 700 is designed to be airtight, allowing the enclosure 700 to contain potentially hazardous chemicals without requiring unnecessary exposure to laboratory personnel during sample preparation or analysis.

As illustrated in FIG. 12, the enclosure 700 includes a first support member 706 and a second support member 708. The first and second support members 706 and 708 are generally perpendicular to a support surface 702 on which the automated sampling/dispensing device is mounted. For example, as illustrated in FIG. 12, the first support member 706 and the second support member 708 are centered generally one hundred and eighty degrees (180°) opposite from one another. Moreover, such support members may be mechanically coupled to the lid 704 of the enclosure 700 as well as to the support surface 702. For instance, fasteners such as screws, bolts, nuts, and so forth may be used to fasten the support members to the lid and support surface. In an implementation, all fasteners are either metal-free or coated with an inert plastic coating to prevent interaction of such fasteners with chemical reagents or other substances being used with the automated sampling/dispensing device. In an additional implementation, an aperture may be formed within one or both of the support members to allow tubes, cords, and so forth to be connected to the automated sampling dispensing device contained within the enclosure as well as to external devices (e.g., laboratory analysis equipment), power sources, and so forth. It is contemplated that the lid 704 as well as the first support member 706 and the second support member 708 may be formed of inert, light-weight material including Plexiglas® (generically known as Lucite or polymethyl methacrylate.)

In additional implementations, as illustrated in FIG. 12, a first flexible sheet 710 and a second flexible sheet 712 are operationally coupled to at least one of the lid 708 or the first support member 706 or the second support member 708. In an implementation, the first flexible sheet 710 includes a first end and a second end. The first end of the first flexible sheet 710 includes a finished edge while the second end of the first flexible sheet 710 is fixedly coupled to the second support member 708. For example, the first end of the flexible sheet 710 is finished with a hardened-plastic cover which extends substantially along the length of the first end of the first flexible sheet 710. In addition, at least one guide member is attached to the first end of the first flexible sheet 710 to allow position of the first flexible sheet to be varied.

Figure 13:
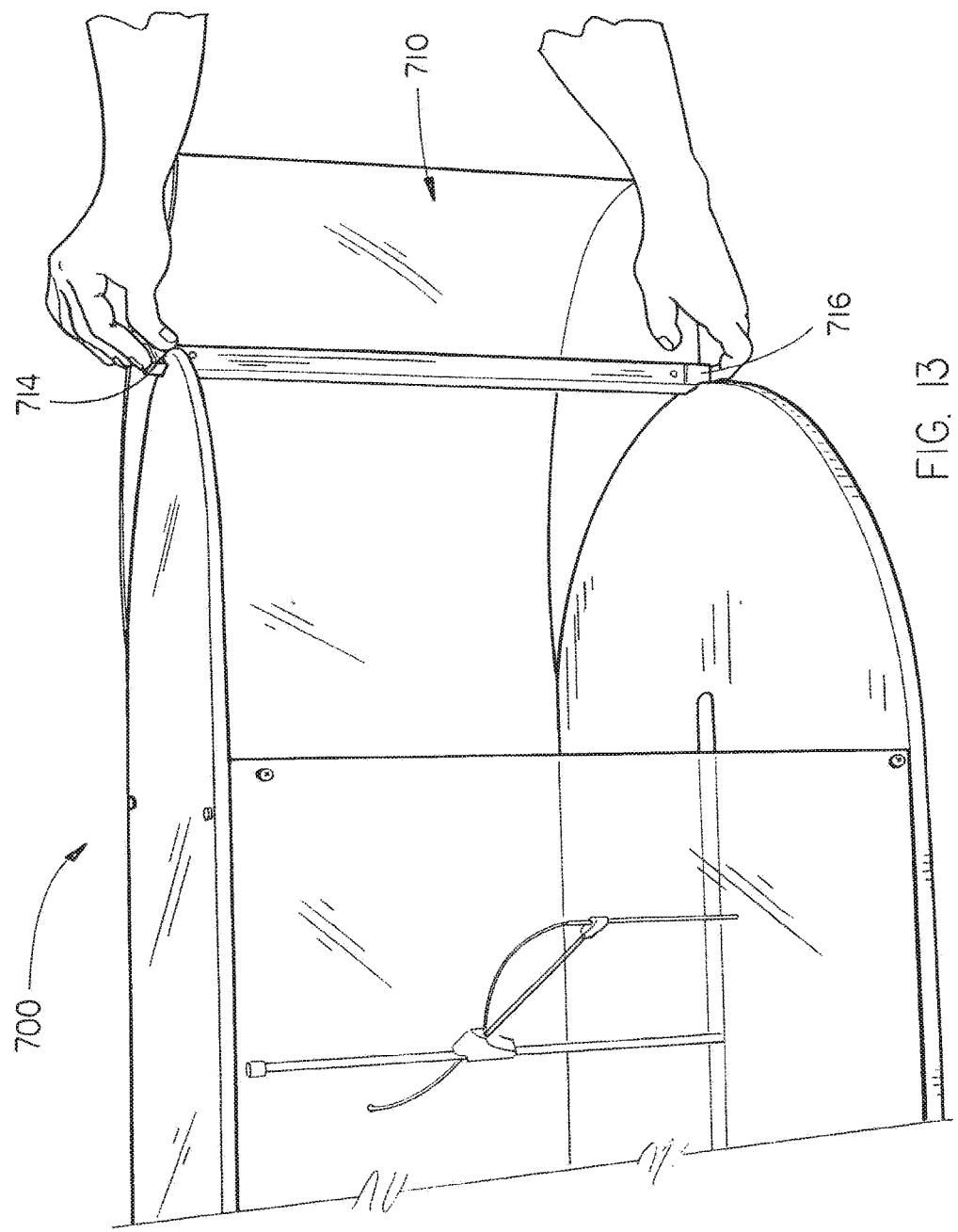
FIG. 13 is a partial front view of the automated sampling or dispensing device enclosure as illustrated in FIG. 12, where one of the flexible sheets of the enclosure is retracted.
Figure 14:
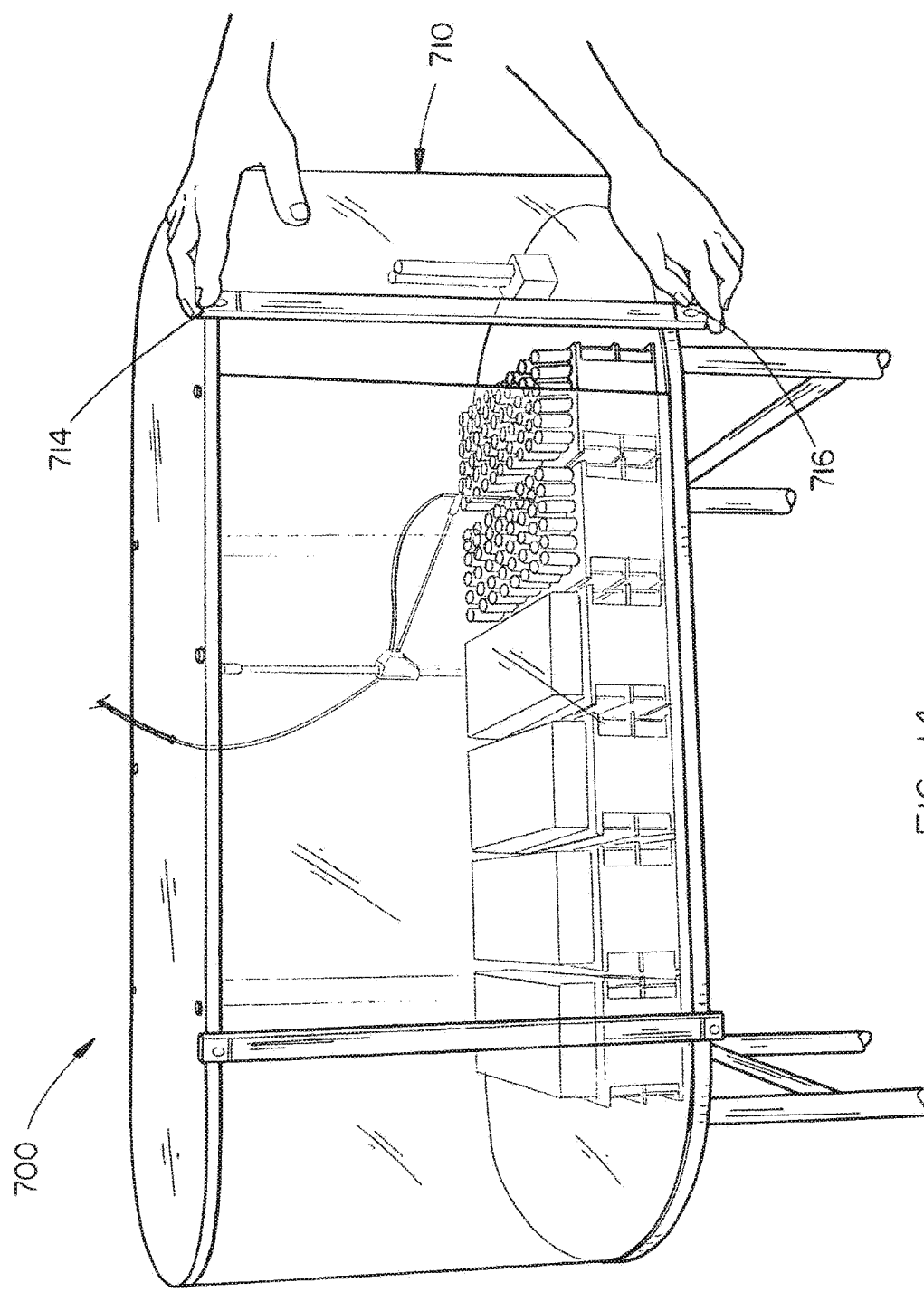
FIG. 14 is a front view of the automated sampling or dispensing device enclosure as illustrated in FIG. 12, where the mechanism of fastening a flexible side shut is demonstrated.

As illustrated in FIGS. 13 and 14, the first end of the first flexible sheet 710 includes a first guide member 714 and a second guide member 716 to allow a user to slide the first flexible sheet 710 along an edge of the support surface 702. In an implementation, the first guide member 714 and the second guide member 716 are press-fit latches allowing a user to secure the flexible sheet at multiple positions along the edge or side of the support surface. For example, a user may release the flexible sheet by applying pressure to the press-fit latches. As illustrated in FIG. 14, a flexible sheet may be moved from a first position to a second position by guiding the first guide member 714 along the edge of the lid 704 while the second guide member is detached from the support surface 710. It is contemplated that additional mechanisms may be employed to guide and secure the flexible sheet at various positions, including fasteners such as clips, pressure-sensitive screws, and so forth. It is further contemplated that a channel may be formed within the support surface to provide an area in which a guide member may slide and be secured.

In the present implementation, the second flexible side 712 includes a first end and a second end. The first end of the second flexible sheet 712 includes a finished edge while the second end of the second flexible sheet 712 is fixedly coupled to the second support member 708. For example, the first end of the second flexible sheet 712 is finished with a hardened-plastic (e.g., Plexiglas®) cover which extends substantially along the length of the first end of the second flexible sheet 712. In addition, at least one guide member is attached to the first end of the second flexible sheet 712 to allow position of the first flexible sheet to be varied. For instance, the first end of the second flexible sheet 712 may include a first guide member 714 and a second guide member 716 to allow a user to slide the second flexible sheet 712 along an edge or side of the support surface 702. In an implementation, the first guide member 714 and the second guide member 716 are press-fit latches allowing a user to secure the flexible sheet at multiple positions along the edge or side of the support surface. It is contemplated that additional mechanisms may be employed to guide and secure the flexible sheet at various positions, including fasteners such as clips, pressure-sensitive screws, and so forth.

Figure 15:
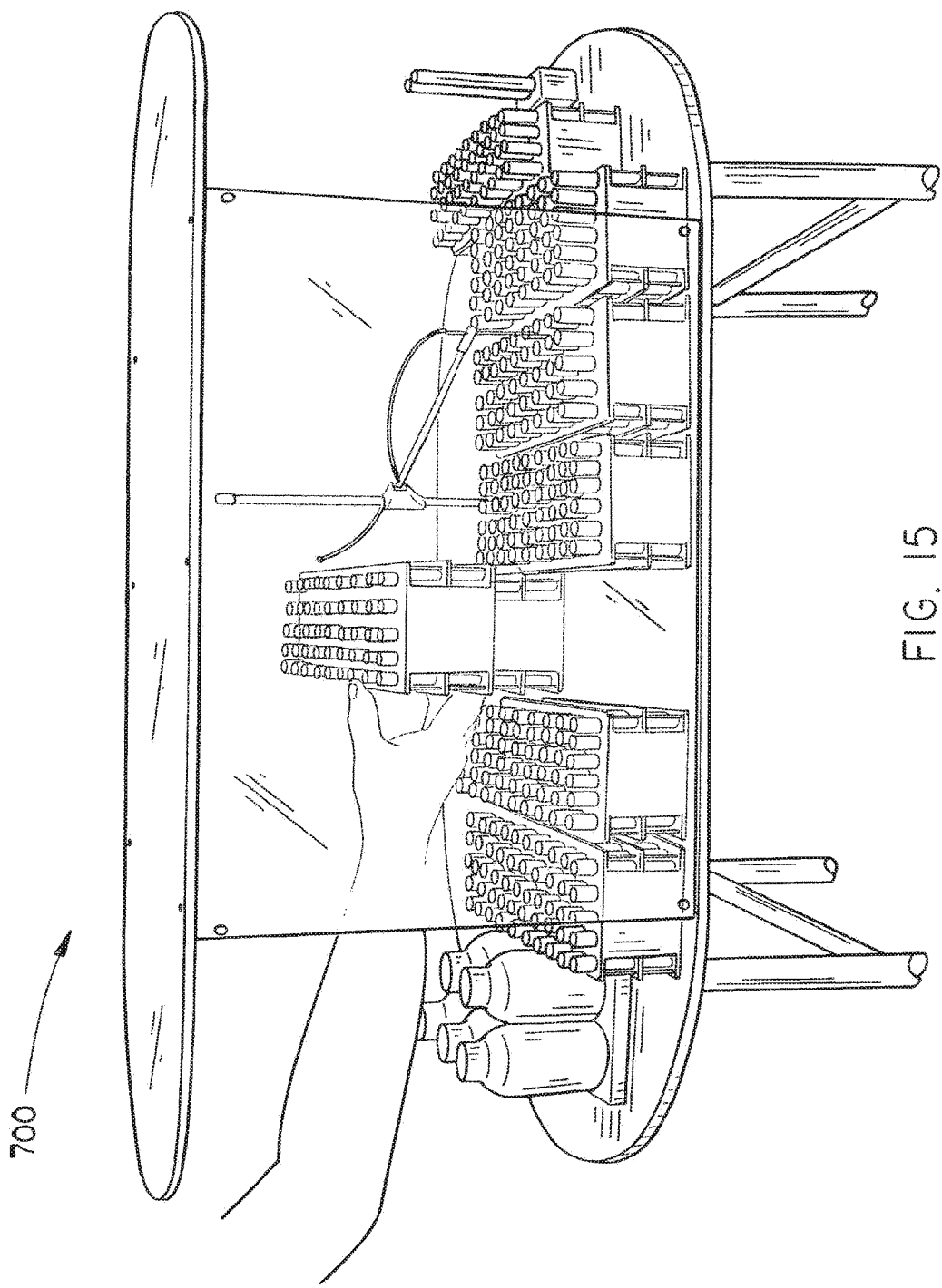
FIG. 15 is a front view of the automated sampling or dispensing device enclosure as illustrated in FIG. 12, where the flexible sheets have been removed.

Referring to FIG. 15, the first and second flexible sheets have been removed to allow access to the support surface 702. In an implementation, the first and second flexible sheets are detachable. The detachable features of such sheets allow a user to load or remove samples efficiently from the support surface 702 so that a user does not have to reposition the sheets in order to gain access to a support surface area. It is contemplated that one or both sheets may be removed depending upon the needs of the user.

Figure 16:
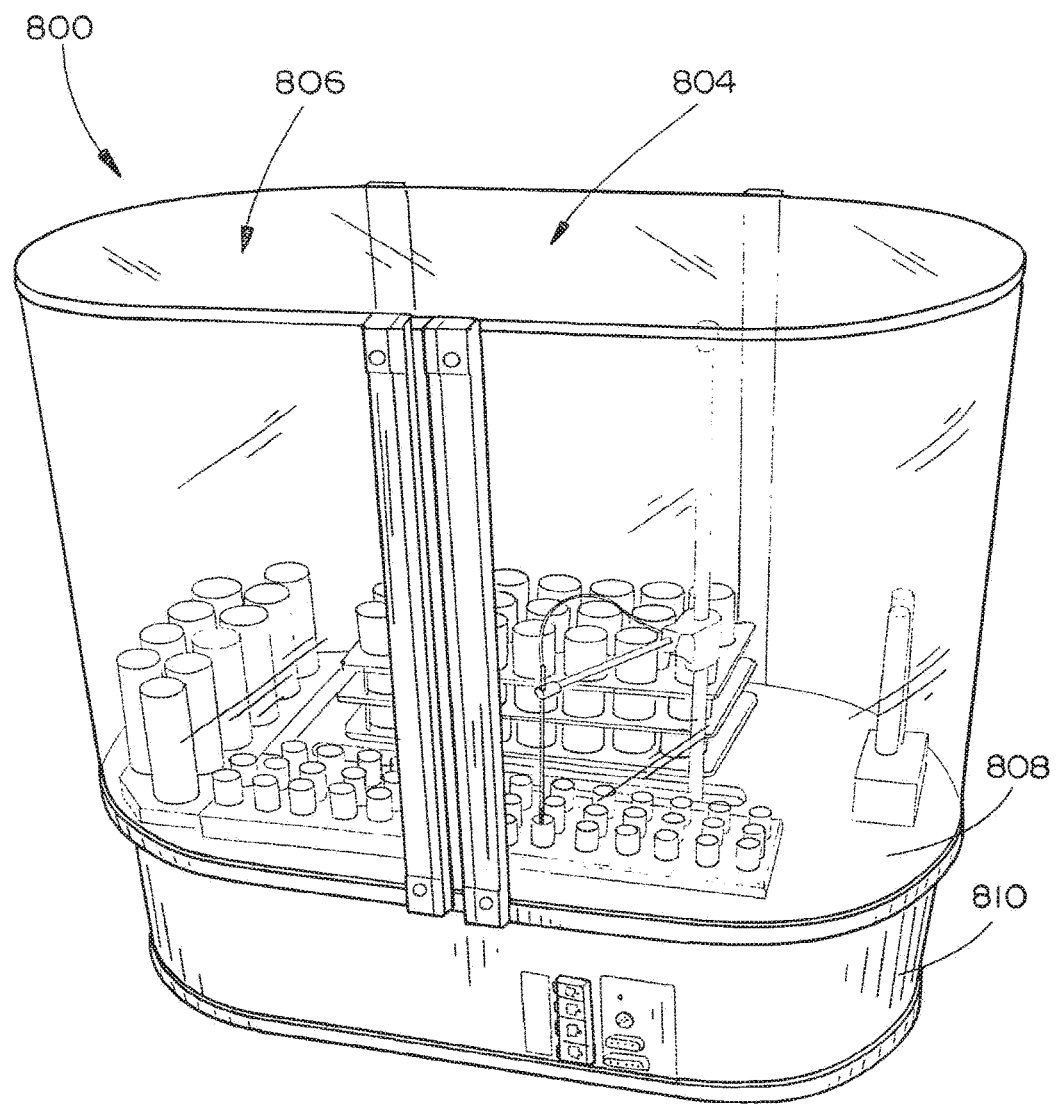
FIG. 16 is an isometric view illustrating an enclosure for a bench top automated sampling or dispensing device in accordance with example implementations of the present disclosure, where the enclosure includes flexible sheets which are in a closed position.
Figure 17:
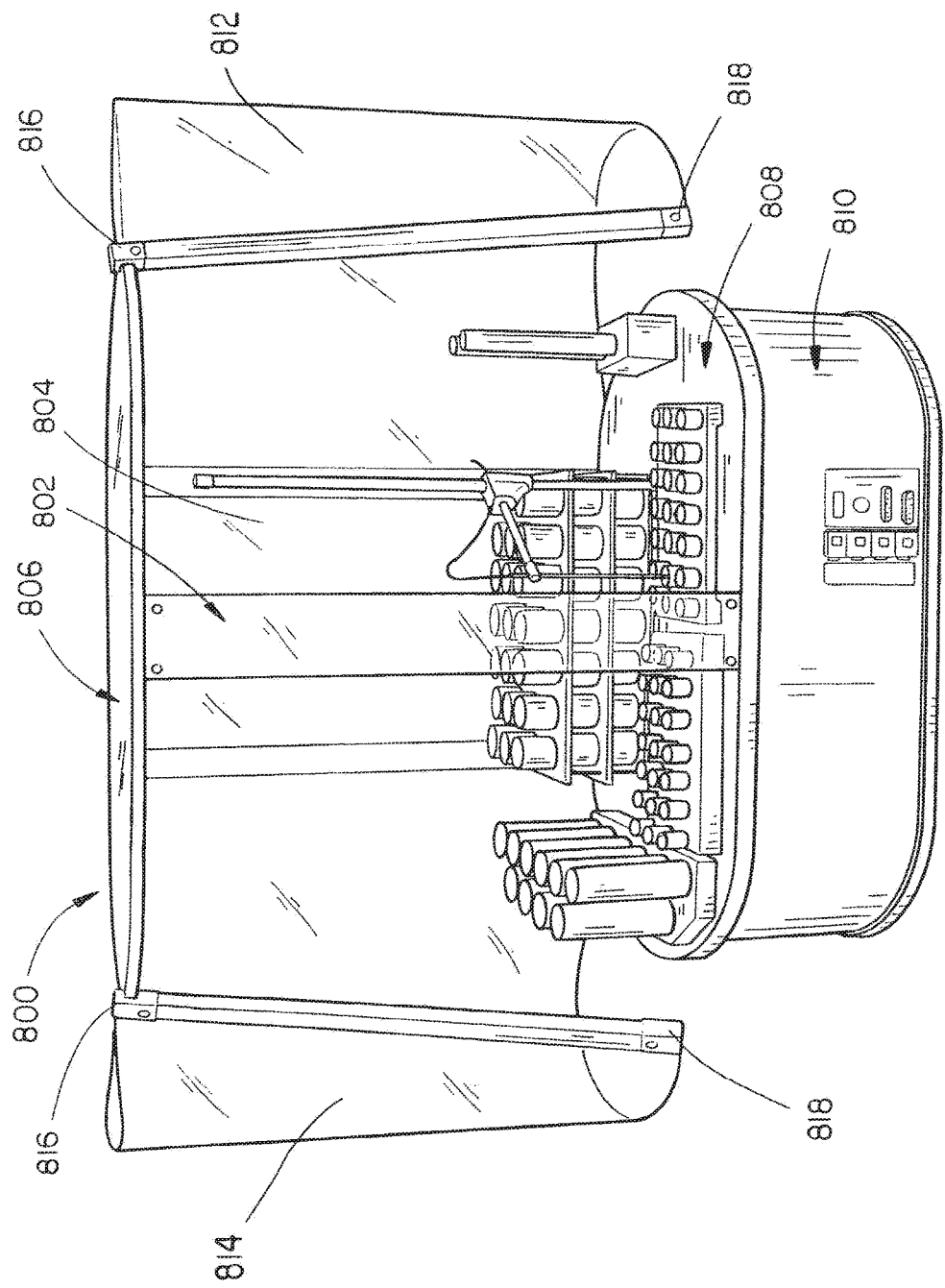
FIG. 17 is a front view of the enclosure for the bench top automated sampling or dispensing device as illustrated in FIG. 16, where the flexible sheets are in an open position.

Referring to FIGS. 16 and 17, an additional example enclosure for enclosing an automated sampling/dispensing device is provided in which the automated sampling/dispensing device is a bench-top automated sampling dispensing device. As illustrated in FIGS. 16 and 17, an enclosure 800 for a bench-top automated sampling dispensing device is configured in a similar manner as the enclosure 700 for a table-top automated sampling/dispensing device. The enclosure 800 includes a first support member 802 and a second support member 804 for supporting a lid 806. In an example implementation, the lid 806 covers a support surface 808 secured to a base 810 of the bench-top automated sampling/dispensing device. In such implementation, the lid 806 is generally equivalent in shape and size to that of the support surface 808, allowing the entire support surface 808 to be enclosed and available for use by a user. Further, the first 802 and second 804 support members are generally perpendicular to the support surface 808.

As illustrated in FIGS. 16 and 17, the first support member 802 and the second support member 804 are centered generally one hundred and eighty degrees (180°) opposite from one another. For example, the first support member 802 is positioned on the front side of the automated sampling/dispensing device (the front side defined as the side including a user power control panel) while the second support member 804 is positioned generally opposite the first support member 802 (e.g., to the rear side of the automated sampling/dispensing device). Moreover, such support members may be mechanically coupled to the lid 806 of the enclosure 800 as well as to the support surface 808. For instance, fasteners such as screws, bolts, nuts, and so forth may be used to fasten the support members to the lid and support surface. In an implementation, all fasteners are either metal-free or coated with an inert plastic coating to prevent interaction of such fasteners with chemical reagents or other substances being used with the automated sampling/dispensing device.

It is contemplated that the lid 806 as well as the first support member 802 and the second support member 804 may be formed of inert, light-weight material including Plexiglas®. It is further contemplated that the enclosure 800 may include an aperture within the lid or at least one of the support members allowing for the automated sampling/dispensing device to be connected with devices external to the enclosure. For example, an aperture may be defined within the lid for allowing a supply tube to the automated sampling/dispensing device to be connected with external laboratory analysis equipment. In another implementation, the enclosure 800 is designed to be airtight allowing the enclosure to contain potentially harmful chemicals without requiring unnecessary exposure to laboratory personal during sample preparation or analysis.

In additional example implementations, as illustrated in FIG. 17, a first flexible sheet 812 and a second flexible sheet 814 are coupled to at least one of the lid 806 or the first support member 802 or the second support member 804. In an implementation, each flexible sheet includes a first and second end. The first end of each flexible sheet includes a finished edge while the second end of each flexible sheet is fixedly coupled to the second support member 804. For example, the first end of the flexible sheet 812 is finished with a hardened-plastic cover (e.g., Plexiglas®) which extends substantially along the length of the first end of the first flexible sheet 812.

In further example implementations, at least one guide member is attached to the first end of each flexible sheet to allow the position of each flexible sheet to be varied. As illustrated in FIG. 17, the first end of each flexible sheet includes a first guide member 816 and a second guide member 818 to allow a user to slide each sheet along an edge of the lid 806 or support surface 808. In an implementation, the first guide member 816 and the second guide member 818 are press-fit latches allowing a user to secure the flexible sheet at multiple positions along the edge or side of the lid or support surface. For example, a user may release the flexible sheet by applying pressure to the press-fit latches. As illustrated in FIG. 17, a flexible sheet may be moved from a first position to a second position by guiding the first guide member 816 along the edge of the lid 806 while the second guide member 818 is detached from the support surface 808. It is contemplated that additional mechanisms may be employed to guide and secure the flexible sheet at various positions, including fasteners such as clips, pressure-sensitive screws, and so forth. It is further contemplated that a channel may be formed within the support surface to provide an area in which a guide member may slide and be secured.

It is contemplated that the first and second flexible sheets may be detachable. The detachable features of such sheets allow a user to load or remove samples efficiently from the support surface 808 so that a user does not have to reposition the sheets in order to gain access to a support surface area. It is contemplated that one or both sheets may be removed depending upon the needs of the user.

Figure 18:
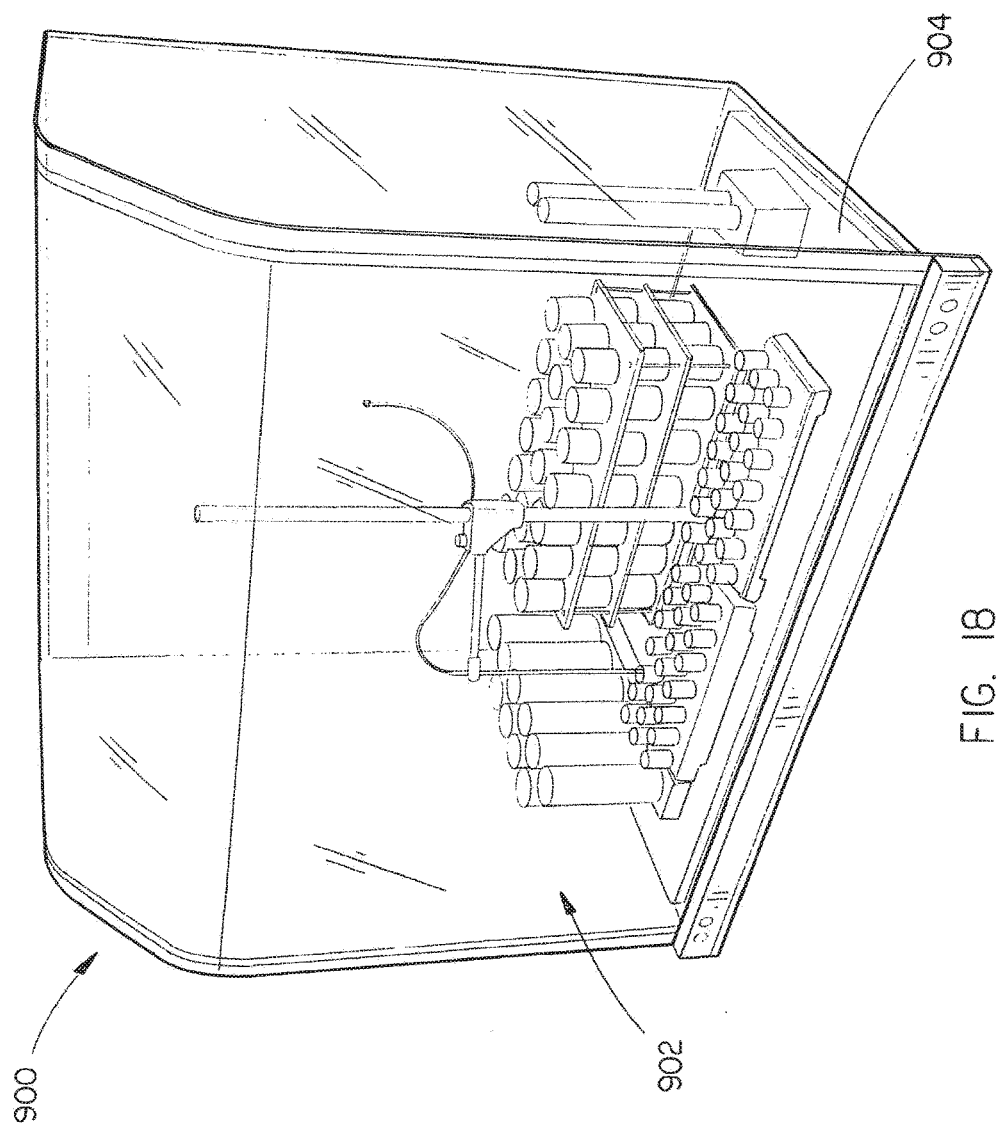
FIG. 18 is an isometric view illustrating an enclosure for an automated sampling or dispensing device in accordance with example implementations of the present disclosure, where the enclosure includes a single flexible front sheet.
Figure 19:
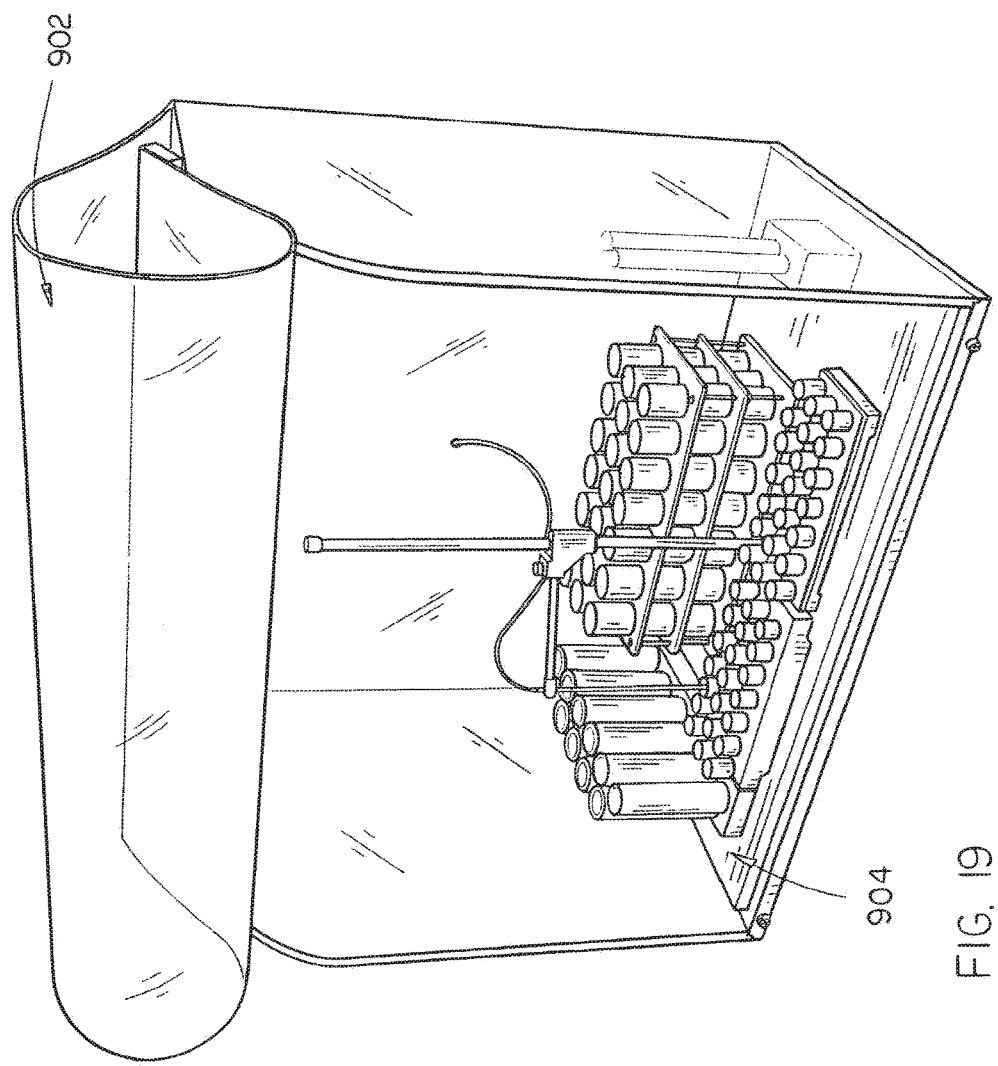
FIG. 19 is an isometric view of the enclosure for the automated sampling or dispensing device as illustrated in FIG. 18, where the front sheet is retracted allowing access to the device.

Referring to FIGS. 18 and 19, a further example enclosure 900 for enclosing an automated sampling/dispensing device is provided in which the enclosure 900 includes a single flexible sheet or panel 902. As illustrated in FIGS. 18 and 19, the enclosure 900 includes a plurality of support walls and a single flexible sheet 902 for enclosing the automated sampling/dispensing device mounted on a support surface 904. For example, the enclosure 900 may include three support walls and the single flexible sheet 902. In such example, a first side support wall and a second side support wall provide support to a rear support wall in which the rear support wall is secured to an edge of the first side support wall and an edge of the second side support wall. The rear support wall is generally opposite to that of the front of the enclosure (e.g., where the front of the enclosure includes the flexible sheet and is used to gain access to the automated sampling/dispensing device). The first and second side support walls are configured to allow the flexible sheet to be rolled along an outer edge of the first side support wall and an outer edge of the second side support wall. It is contemplated that an aperture may be defined within at least one of the plurality of walls for allowing the enclosed apparatus to be connected with external devices or power sources.

With continued reference to FIGS. 18 and 19, the single flexible sheet 902 includes a first and second edge. The first end of the flexible sheet 902 includes a finished edge while the second end of the flexible sheet 902 is fixedly coupled to the rear support wall. For example, the first end of the flexible sheet 902 is finished with a hardened-plastic cover which extends substantially along the length of the first end of the flexible sheet 902. To gain access to the interior of the enclosure 900, the single flexible sheet 902 may be retracted with a first end of the first edge of the single flexible sheet 902 being secured to the outer edge of the first side support wall and a second end of the first edge being secured to the outer edge of the second side support wall. It is contemplated that various mechanisms may be employed to secure the first edge of the flexible sheet 902 to the side support edges including press fit latches, clips, screws, and so forth. In addition, the enclosure 900 may be mounted to an automated sampling/dispensing device for laboratory analysis equipment in which the enclosure may be positioned to enclose such device by securing the enclosure to a support area supporting the device. Moreover, the single flexible sheet may be detachable allowing a user access to the entire support surface area as well as to the over-head support surface area.

Although the presently described enclosure focuses upon the use of such enclosure with an automated sampling/dispensing device, it is contemplated that such enclosure may be employed with a variety of laboratory equipment in accordance with the present disclosure. It is further contemplated that example enclosures may be ventilated to prevent the entry of contaminates such as bacteria or air-borne substances into the external environment. For instance, the air drawn into the enclosure can be passed through a HEPA filter.

Figure 20:
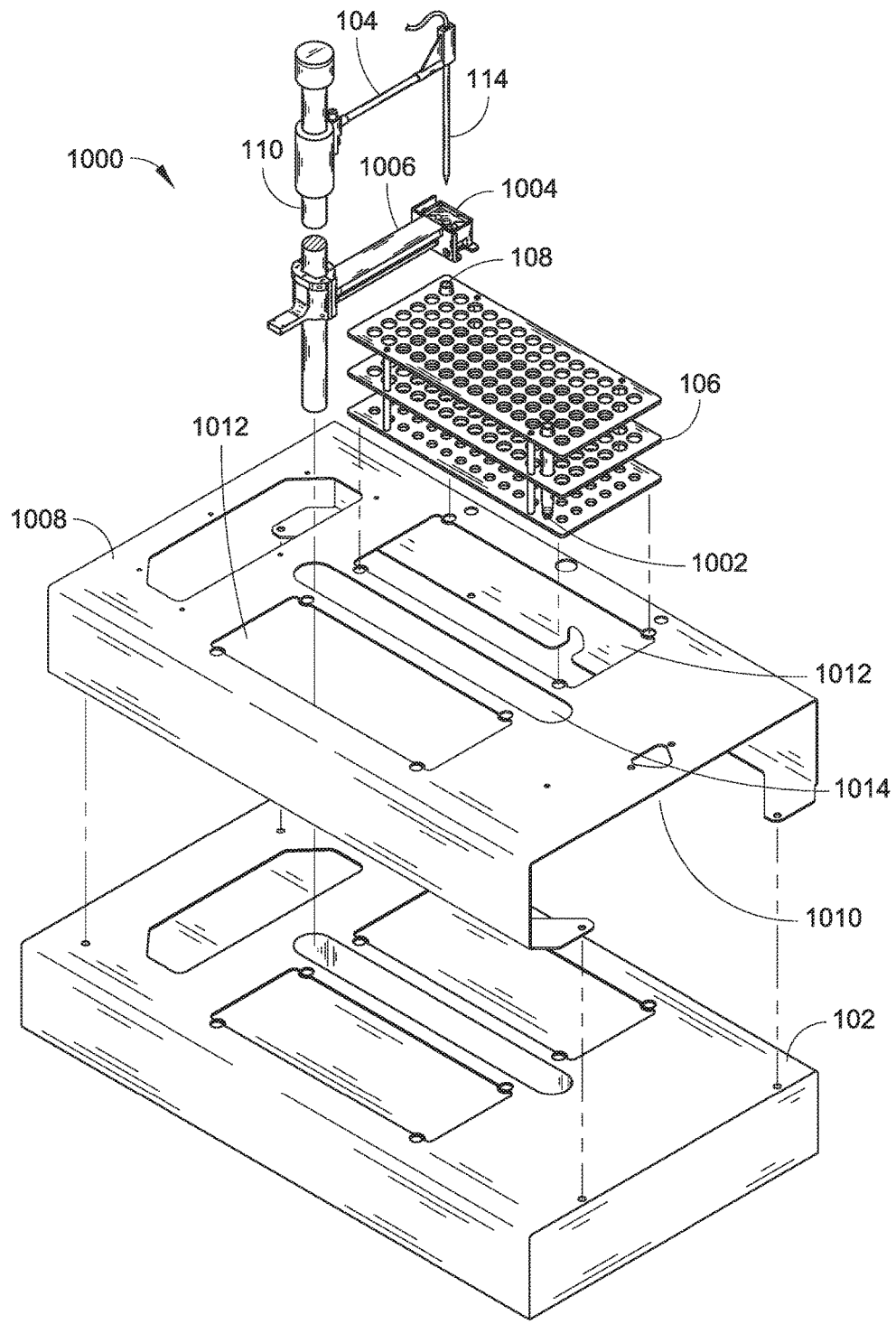
FIG. 20 is a partially exploded isometric view of an automated sampling or dispensing device having a sample identification system in accordance with example implementations of the present disclosure.

Referring now to FIG. 20, a sample identification system 1000 for an automated sampling or dispensing device is shown in accordance with an example implementation of the pressure disclosure. The sample identification system 1000 is configured to verify a sample identity before, during, and/or after sampling and/or dispensing by the automated sampling or dispensing device occurs. As illustrated, the sample identification system 1000 includes a sample identifier 1002 and an identifier capture device 1004. The sample identifier 1002 is configured to provide indicia of the sample, such as a sample positioned in a particular location with respect to the autosampler table top (e.g., table top 102). The sample identifier 1002 may be configured for placement on the autosampler table top, on a sample holder (e.g., sample holder 106), on a sample vessel (e.g., sample vessel 108), or another location for reading by the identifier capture device 1004. In an implementation, the sample identifier 1002 is located on a base or bottom of a sample vessel (e.g., sample vessel 108), such as on the bottom of a test tube, such that the identifier capture device 1004 can access the sample identifier 1002 for processing/imaging of the sample identifier 1002 from a position beneath the sample vessel. In an implementation, the sample identifier 1002 includes a barcode configured for recognition by an optical reader (e.g., a barcode reader), where the barcode is configured to represent a particular sample according to one or more identifiers, including but not limited to, a position within a test rack, a position with respect to a table top, a particular identification number corresponding to a predetermined sampling order of sample vessels, and so forth. The barcode can include a data matrix two-dimensional (2D) barcode, such as a 12×12 matrix, a 13×13 matrix, a 14×14 matrix, or any other suitable matrix. While square matrices are provided as example data matrix barcodes, it is contemplated that rectangular matrices also may be utilized. The sample identifier 1002 can include other identification indicia including, but not limited to: characters and/or patterns configured for recognition by an optical camera or sensor; raised surfaces for recognition by touch sensors, optical sensors, and the like; illumination sources configured to generate a particular color (or wavelength), pattern of light, etc.; other identification indicia configured for recognition by the identifier capture device 1004; and so forth.

In an example implementation, the sample identification system 1000 includes an identifier arm assembly 1006 (which may be separate from or include the sample arm assembly 104) supported by a z-axis support (which may be separate from or include the z-axis support 110). In an implementation, the identifier arm assembly 1006 is configured to move vertically with respect to the z-axis support (shown as 110 in FIG. 20). As illustrated in FIG. 1, the z-axis is aligned with gravity or a vertical axis. The identifier arm assembly 1006 may include the identifier capture device 1004 mounted thereto, such that the identifier capture device 1004 can move to capture/image the sample identifier 1002 of various samples supported by the autosampler table top 102, a sample holder (e.g., sample holder 106), or other support surface. In use, identifier arm assembly 1006 is configured to be moved through space in three dimensions, or about an axis having y-motion that is a substantially rotary motion and along an axis having x-motion which is an at least substantially horizontal linear motion or translation, and along a z-axis that is an at least substantially vertical, linear motion or translation. As such, the identifier arm assembly 1006 may be configured for movement through an R-theta range of motion, an x-y range of motion, and the like, such as between a rest position and an operating position configured to image sample vessels including sample identifiers 1002. In an implementation, the identifier arm assembly 1006 is configured to move independently from the sample arm assembly 104.

Figure 21A:
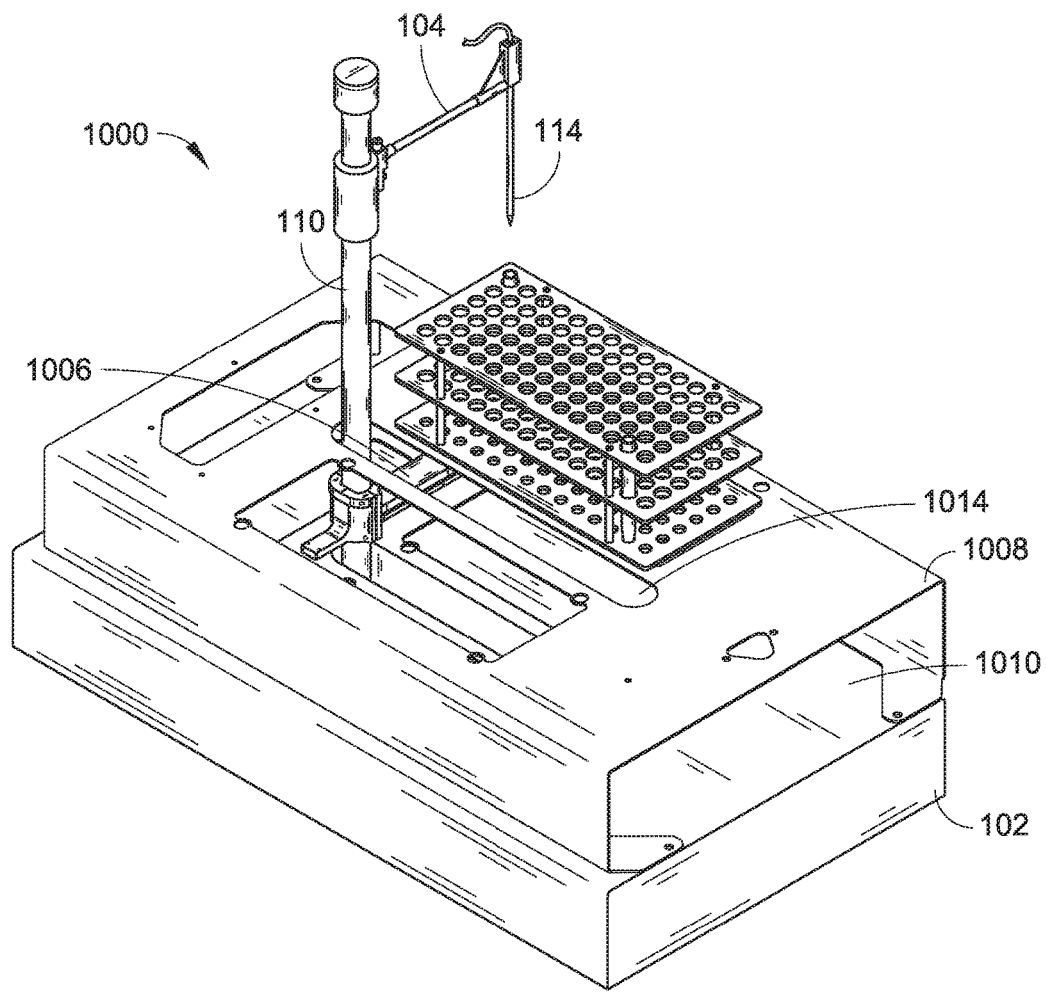
FIG. 21A is an isometric view of the automated sampling or dispensing device of FIG. 20.
Figure 21B:
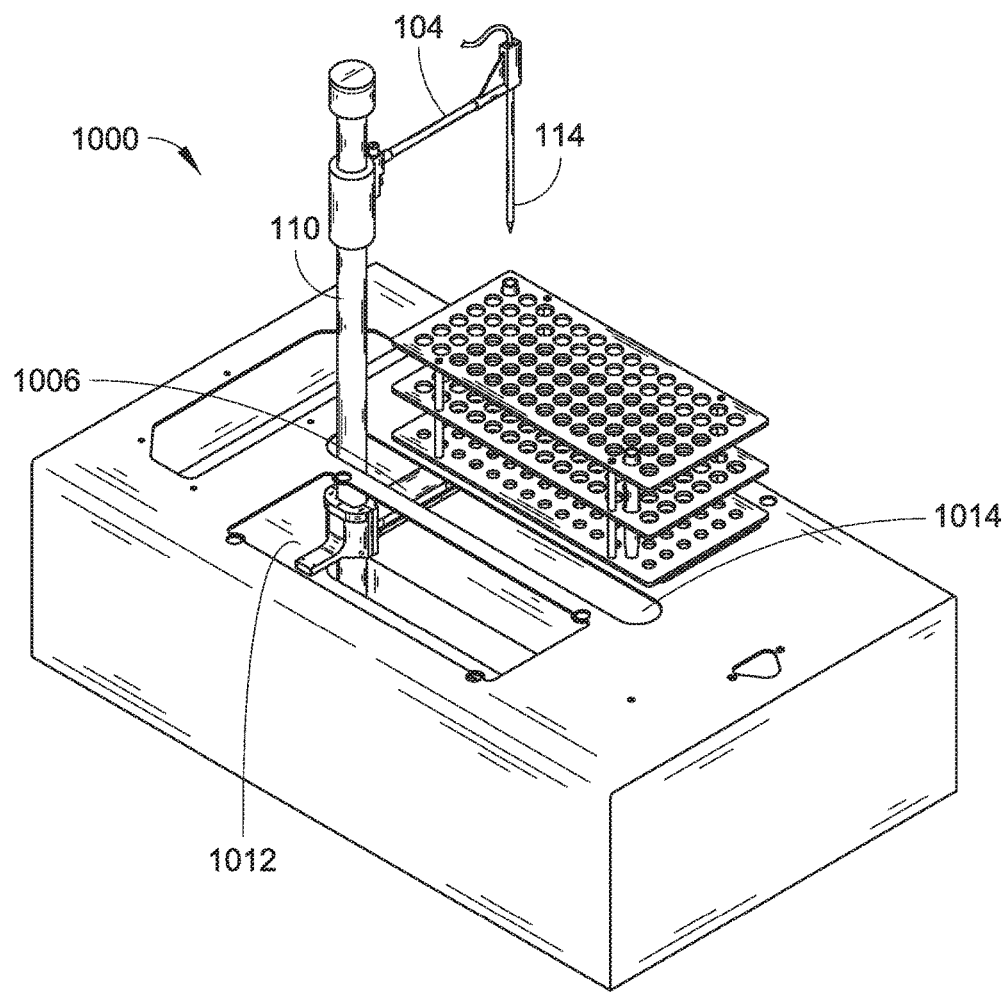
FIG. 21B is an isometric view of an automated sampling or dispensing device having a sample identification system in accordance with example implementations of the present disclosure.
Figure 21C:
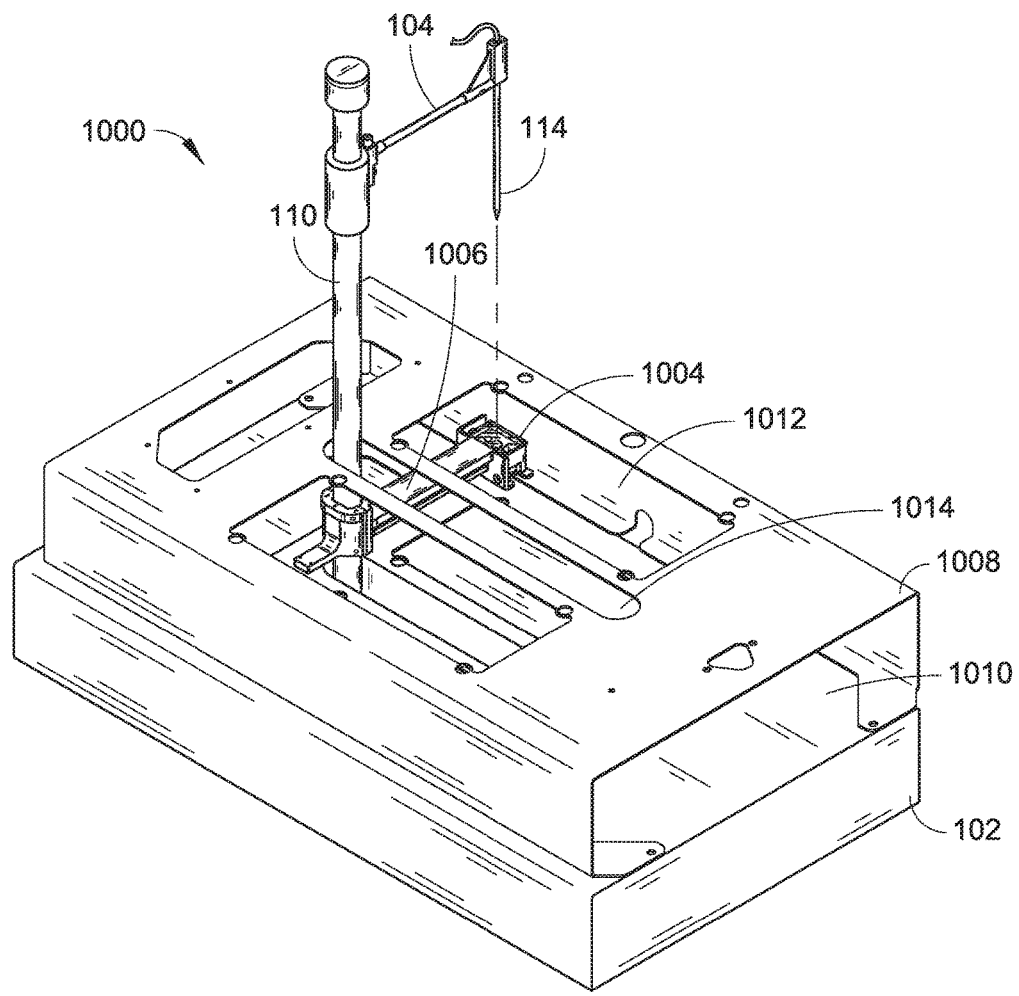
FIG. 21C is an isometric view of the automated sampling or dispensing device of FIG. 20 shown in an operating position.
Figure 22:
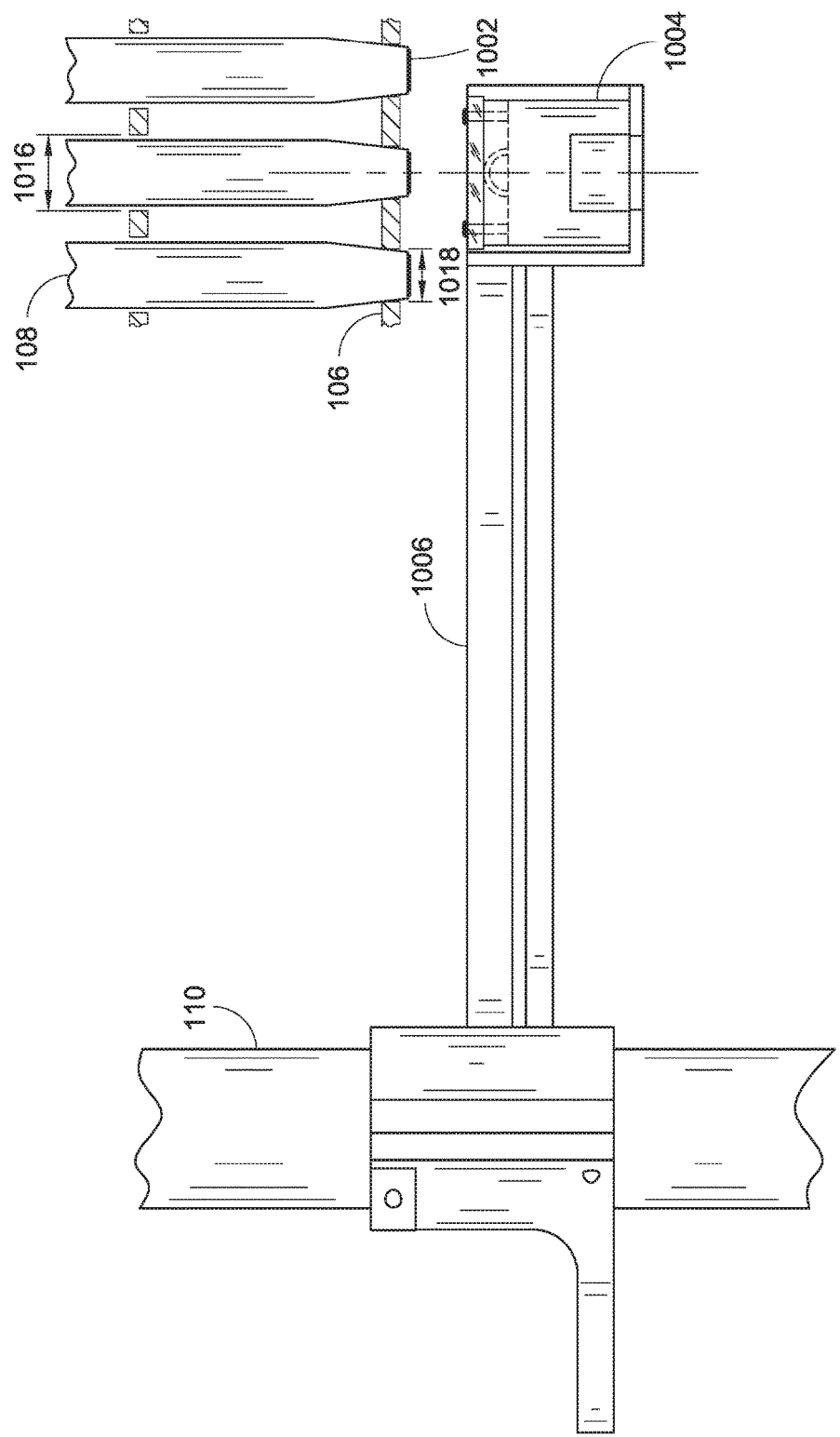
FIG. 22 is a partial side view of an identifier arm assembly in position beneath a sample holder having sample vessels with sample identifiers.

In an implementation, as shown in FIG. 20, the autosampler includes a raised surface 1008 configured to be supported by the autosampler table top 102. The raised surface 1008 can support sample holders and sample vessels for access by the sample probe 114. The raised surface 1008 may be positioned with respect to the table top 102 such that the raised surface 1008 and the table top 102 define a gap 1010 into which the identifier arm assembly 1006 and identifier capture device 1004 can enter for access to the underside of the sample vessels (e.g., sample vessels 108) and associated sample identifiers 1002. For instance, in implementations, the raised surface 1008 defines gaps 1012 in the surface over which the sample vessels 108 having sample identifiers 1002 positioned on a bottom surface are situated. In this manner, the sample identifiers 1002 at the base or bottom of the sample vessels 108 are accessible to the identifier capture device 1004 when positioned beneath the raised surface 1008 in the gap 1010 (such as shown in FIG. 22). The raised surface 1008 can also define a center slot 1014 to correspond to at least a portion of the center slot 120 of the table top 102 to permit motion of the sample arm assembly 104 across the raised surface 1008 and the corresponding portion of the table top 102 (such as shown in FIGS. 21A through 21C).

Figure 23A:
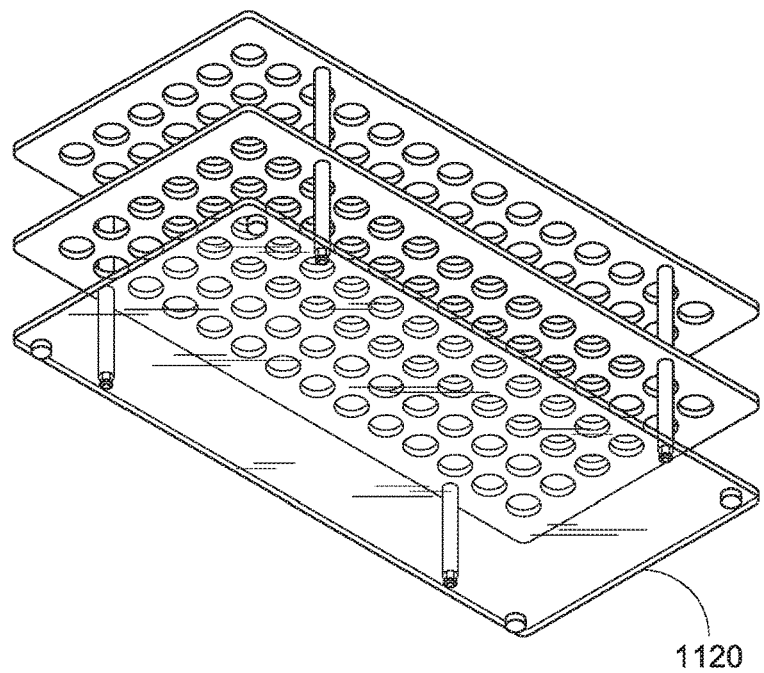
FIG. 23A is an isometric view of a sample holder including a substantially transparent bottom.
Figure 23B:
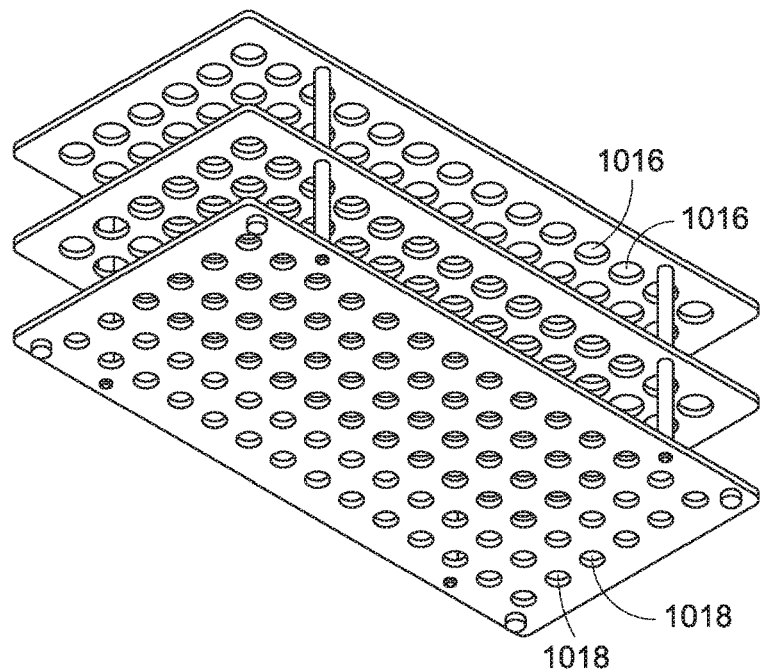
FIG. 23B is an isometric view of a sample holder including a first set of apertures configured to hold sample vessels and a second set of apertures on a bottom portion of the sample holder.

In example implementations, the autosampler includes sample holders (e.g., sample racks 106) configured to permit the identifier capture device 1004 to read the sample identifier 1002. For example, a base of the sample holders 106 may be constructed from a substantially clear, light transmissive, or transparent material. In other embodiments, the sample holder 106 may be constructed with an open bottom. Use of a light transmissive or transparent material may protect the identifier capture device 1004 from inadvertent contact with sample fluids within the sample vessels 108. In an implementation, the sample holders are formed of, or are coupled with, a material configured to reduce or eliminate glare associated with light when utilizing the identifier capture device 1004. Alternatively or additionally, the identifier capture device 1004 can include a protective coating or covering to protect the identifier capture device 1004 from inadvertent contact with the sample fluids. Such coating or covering of may be configured to reduce or eliminate glare associated with light when utilizing the identifier capture device 1004. In an implementation (such as shown in FIG. 23A), the sample holder 106 includes a substantially transparent bottom 1120, through which the image capture device 1004 can recognize the sample identifier 1002 on a base of a sample vessel 108 supported by the sample holder 106. In an implementation (such as shown in FIGS. 22 and 23B), the sample holder 106 defines a first set of apertures 1016, through which the sample vessels 108 may pass, and a second set of apertures 1018 which prohibit at least a portion of the sample vessels 108 from completely passing through. For instance, the first set of apertures 1016 can have a larger cross-sectional area (e.g., larger diameter with larger circular cross-sectional area) than the second set of apertures 1018, where the second set of apertures 1018 have a cross-sectional area that is smaller than a cross-sectional area of the sample vessels 108 (e.g., the diameter of the second set of apertures 1018 is less than the diameter of a portion of the sample vessels 1018). Such a configuration of apertures may provide an exposed bottom portion of the sample vessel 108 such that the sample identifier 1002 is unobstructed with respect to the identifier capture device 1004. In an example implementation, the sample holder 106 includes a raised base, such that the sample vessels 108 within the holder 106 are positioned over the autosampler table top 102 with a gap between the base of the sample holder 106 and the autosampler table top 102. Such a configuration may permit the identifier capture device 1004 access beneath the sample holder to read the sample identifier 1002. It is contemplated that the size, shape, and materials comprising the sample holder 106 may vary depending on the type, size, and shape of the identifier capture device 1004 used in the sample identification system 1000, and the type of samples to be analyzed (e.g., corrosive, inert, and so forth).

Figure 24:
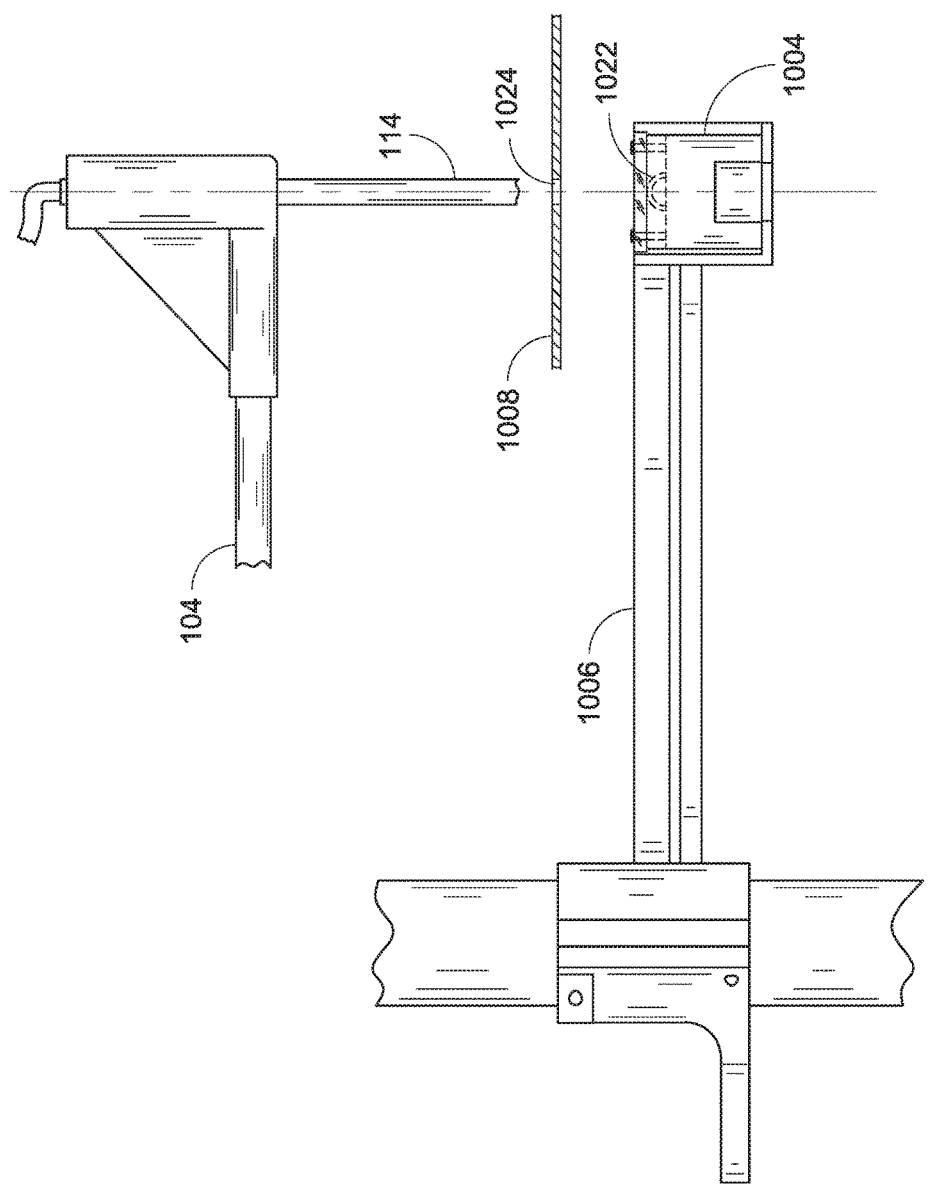
FIG. 24 is a partial side view of an identifier capture device and a sample probe, where the identifier capture device is aligned with the sample probe.

The autosampler may be configured to align the identifier capture device 1004 with the sample probe 114. For example, as shown in FIG. 24, the identifier capture device 1004 includes an alignment light source 1022 configured to project light (e.g., a light beam) toward the sample probe to provide a visual indication of an alignment of the identifier capture device 1004 with the sample probe 114. In an implementation, the raised surface 1008 defines an aperture 1024 through which the alignment light source 1022 can project the light toward the sample probe 114. Where the positioning of the sample probe 114 with respect to the identifier capture device 1004 is not aligned, one or more of the sample arm assembly 104 and the identifier arm assembly 1006 can be repositioned until the alignment is satisfactory. The repositioning can be accomplished through an automatic, motorized movement of the sample arm assembly 104 and the identifier arm assembly 1006 (e.g., through control of drive assembly 100) or through manual means. For example, one or more of the sample arm assembly 104 and the identifier arm assembly 1006 can be secured with a set screw, with press fit, with a friction clamp, and so forth. The alignment may assist in accuracy of the correspondence between the imaged sample identifier 1002 by the identifier capture device 1004 and the actual sample drawn by the sample probe 114 from the sample vessel 108.

Figure 25:
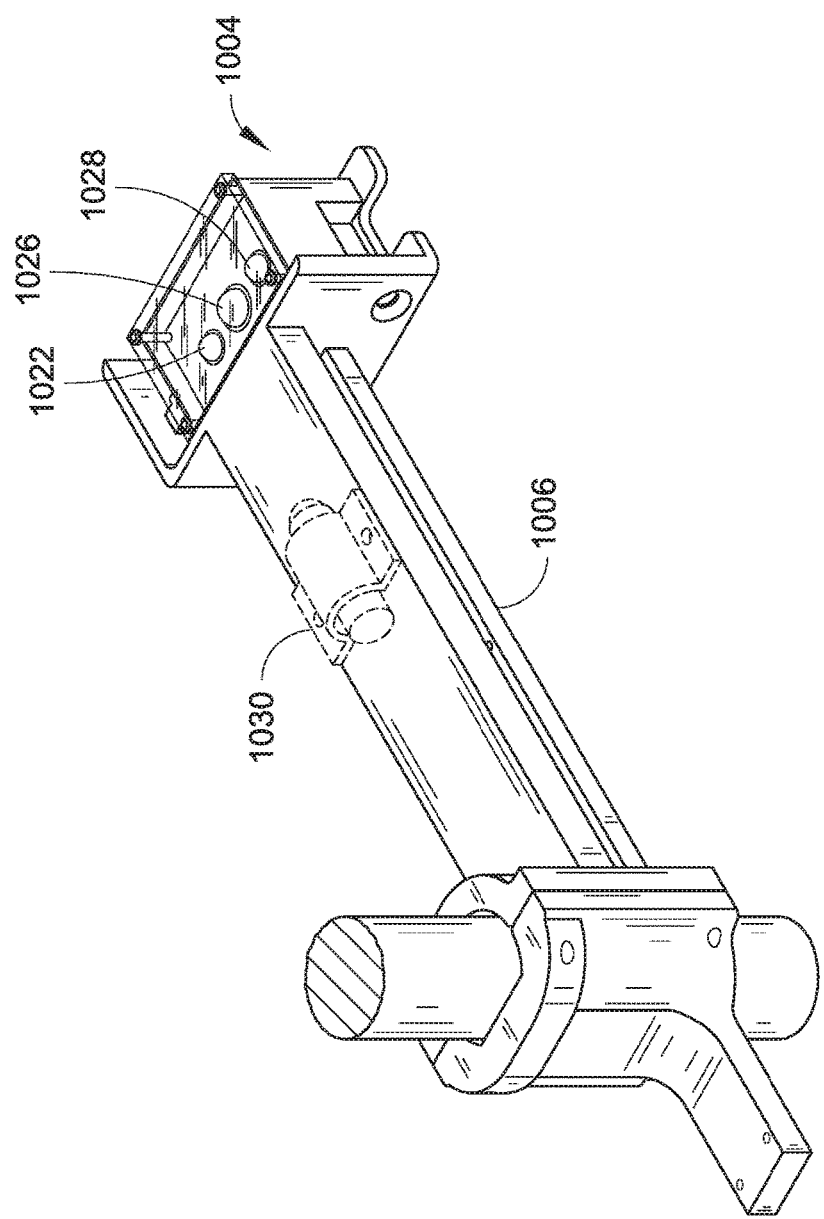
FIG. 25 is an isometric view of an identifier arm assembly having an identifier capture device.

The identifier capture device 1004 is configured to capture, image, or otherwise recognize the sample identifier 1002. Accordingly, in an implementation such as shown in FIG. 25, the identifier capture device 1004 includes an imaging device 1026, a light source 1028 (e.g., a flash source), and the alignment light source 1022. The imaging device 1026 can capture video images of the sample identifiers 1002 and surrounding areas, such that the imaging device 1026 can be associated with a display for displaying the captured images, such as on a live or continuous basis. In an implementation, the imaging device is configured to provide still images of a target. The light source 1028 may be configured to illuminate the bottom of the sample vessels 108 such that the sample identifier 1002 has increased visibility to the imaging device 1026 in order to image the sample identifier 1002. In an implementation, the identifier capture device 1004 is aided by an external light source 1030 to provide illumination in addition to or instead of the light source 1028. For example, the external light source 1030 can be mounted on the identifier arm assembly 1006.

Figure 26A:
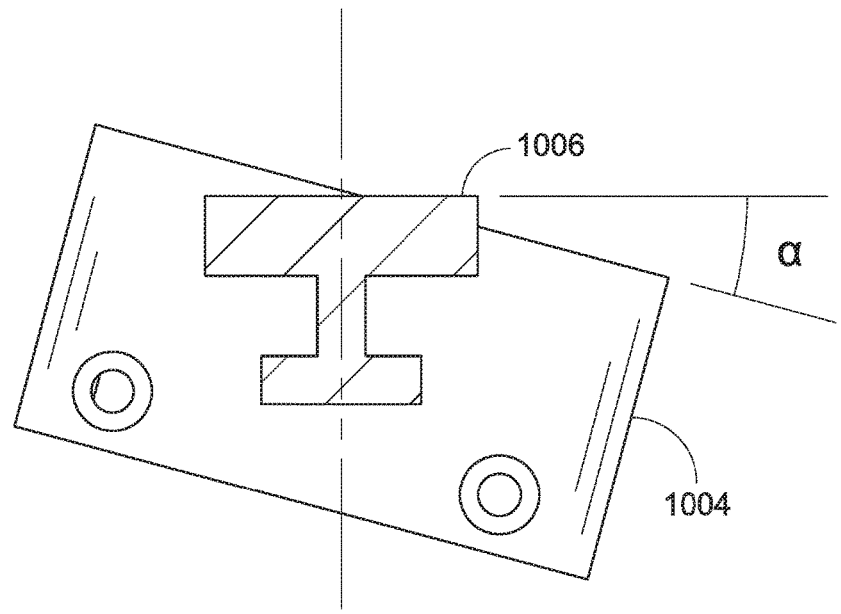
FIG. 26A is a side view of an identifier arm assembly relative to an identifier capture device for a system, such as the system shown in FIG. 20, where the identifier arm assembly is positioned substantially perpendicular to the alignment axis, and where the identifier capture device is positioned at an angle from perpendicular to the alignment axis.
Figure 26B:
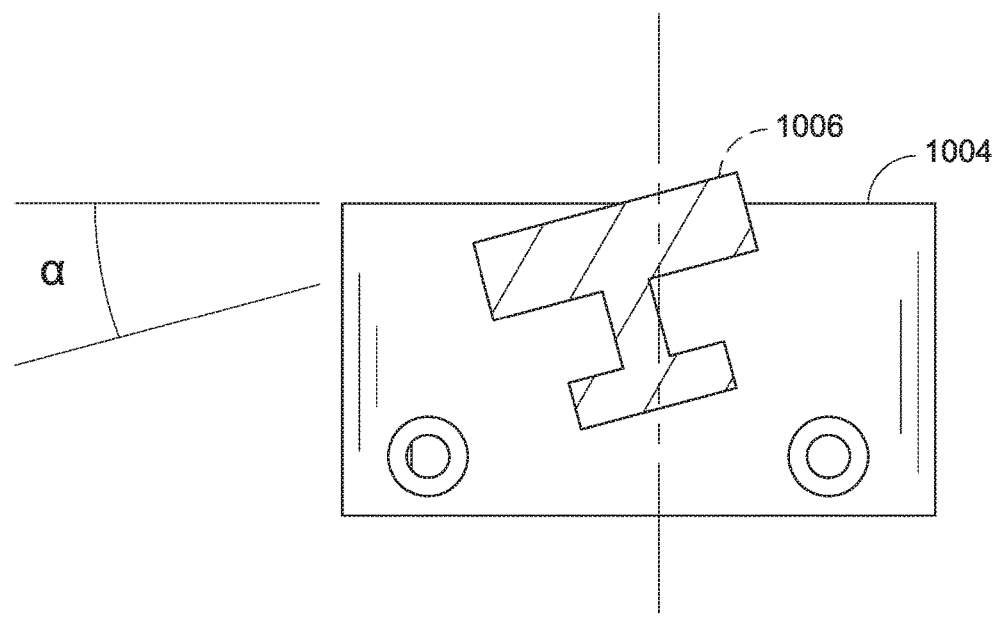
FIG. 26B is a side view of an identifier arm assembly relative to an identifier capture device for a system, such as the system shown in FIG. 20, where the identifier capture device is positioned substantially perpendicular to the alignment axis, and where the identifier arm assembly is positioned at an angle from perpendicular to the alignment axis.

In implementations, the identifier capture device 1004 is angled relative to the identifier arm assembly 1006, such that the imaging device 1026 views the sample identifier 1002 on the base of the sample vessel 108 at an angle from the horizontal or with respect to the orientation of the autosampler table top. For example, as shown in FIG. 26A, the identifier capture device 1004 and the identifier arm assembly 1006 are oriented at an angle of alpha ($\alpha$) (e.g., 15 degrees) relative to each other, where a top surface of the identifier arm assembly 1006 is substantially perpendicular to the alignment axis (e.g., substantially parallel to the surface of table top). In FIG. 26B, the identifier capture device 1004 and the identifier arm assembly 1006 are oriented at an angle of alpha ($\alpha$) (e.g., 15 degrees) relative to each other, where a top surface of the identifier capture device 1004 is substantially perpendicular to the alignment axis (e.g., substantially parallel to the surface of table top). Various configurations of the angle are contemplated, where the angle utilized may depend on the particular imaging device 1026 utilized in the identifier capture device 1004.

The sample identification system 1000 is configured to verify data associated with the sample identifier 1002, and correspondingly, the sample uniquely associated with the sample identifier 1002, before, during, or after sampling of the sample by the autosampler sampling probe (e.g., sample probe 114). The sample identification system 1000 may collect and process data associated with the sample identifier 1002, where the data can include, but is not limited to, the location of a sample (e.g., a location on the autosampler table top 102, a location within a sample rack 106, a particular sample vessel 108, and so forth), a timestamp of when a sample is taken (e.g., by the sample probe 114), presence or absence of a sample, type or extent of analysis to be performed on a sample, dilution factor, and the like. In an implementation, the sample identifier 1002 is read by the identifier capture device 1004 for conversion to a serial number, where data associated with the serial number is associated with the particular sample vessel that includes the sample identifier 1002. In this manner, the sample identifier 1002 can associate data including, but not limited to, the location of a sample, timestamp of when a sample is taken, presence or absence of a sample, type or extent of analysis to be performed on a sample, dilution factor, and the like with a particular sample in the vessel, where the data can be stored in a memory device of a data system to be correlated with the serial number stored by the sample identifier 1002. In an implementation, the sample identification system 1000 can be configured for dilution factor control of a sample. For example, the data associated with a particular sample identifier 1002 can include a dilution factor for offline or online dilution of a sample. In an implementation, the sample identification system 1000 is configured to populate data of prepared samples, such as by filling in standards data into data tables automatically, based on the sample identifier 1002 and the results of a sample analysis by an analyzer (e.g., mass spectrometer, gas chromatograph, liquid chromatograph, and the like) of the particular sample.

The sample identifier 1002 can be associated with and/or comprise information including, but not necessarily limited to: a sample vial identification number, a destination vial identification number, a dilution factor (DF), a final volume, a sample volume, a diluent volume, a diluent location, and so forth. For example, a first barcode is placed on a sample vial and associated with a desired dilution factor and a desired final volume. A destination vial includes a second barcode associated with the first barcode. The system 1000 uses information obtained from the first barcode to dilute a portion of a sample contained in the sample vial. For instance, the system 1000 identifies the destination vial using the second barcode and deposits a portion of the sample into the destination vial. The system 1000 also deposits an amount of diluent sufficient to provide the DF and final volume specified by the first barcode.

In another embodiment, the first barcode is representative of a sample vial identification number, and the sample identification number is associated with a desired dilution factor and a desired final volume. In some embodiments, a user interface (e.g., a graphical user interface) included with an information handling system device operatively coupled with the sample identification system 1000 via a communications interface is used to associate the first barcode with the desired dilution factor and the desired final volume. For instance, the desired dilution factor and the desired final volume can be stored in an electronic database with the first barcode. A destination vial includes a second barcode associated with the first barcode (e.g., via the electronic database). The system 1000 uses information associated with the first barcode in the electronic database to dilute a portion of the sample contained in the sample vial. For instance, the system 1000 identifies the destination vial using the association with the second barcode and deposits a portion of the sample into the destination vial. The system 1000 also deposits an amount of diluent sufficient to provide the DF and final volume specified in the electronic database.

However, these off-line embodiments are provided by way of example only and are not meant to limit the present disclosure. In other embodiments, dilution of a sample can be performed on-line. For example, the system 1000 uses information obtained from a barcode to dilute a portion of a sample contained in the sample vial by mixing the sample portion with an amount of diluent sufficient to provide a desired DF and a desired final volume as specified by a first barcode, associated with the first barcode in an electronic database, and so forth.

The data collected by the sample identification system 1000 may be transferred to another system for identity verification. In an example implementation, the data collected by the sample identification system 1000 is transferred to a laboratory information management system (LIMS) and/or a laboratory instrument to verify the identity of a measured sample. The identifier capture device 1004 may be configured for wired or wireless data transfer between the sample identification system 1000 and the LIMS, laboratory instrument, or other device. In an example embodiment, the identifier capture device 1004 is configured for fiber optic data transfer. The identifier capture device 1004 may be configured for control by the sample identification system 1000 via wired or wireless control mechanisms.

A sample identification system 1000, including some or all of its components, can operate under computer control. For example, a processor can be included with or in a sample identification system 1000 to control the components and functions of systems 1000 described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems 1000. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

A processor provides processing functionality for the system 1000 and can include any number of processors, micro-controllers, or other processing systems, and resident or external memory for storing data and other information accessed or generated by the system 1000. The processor can execute one or more software programs that implement techniques described herein. The processor is not limited by the materials from which it is formed or the processing mechanisms employed therein and, as such, can be implemented via semiconductor(s) and/or transistors (e.g., using electronic integrated circuit (IC) components), and so forth.

The system 1000 also includes a memory. The memory is an example of tangible, computer-readable storage medium that provides storage functionality to store various data associated with operation of the system 1000, such as software programs and/or code segments, or other data to instruct the processor, and possibly other components of the system 1000, to perform the functionality described herein. Thus, the memory can store data, such as a program of instructions for operating the system 1000 (including its components), and so forth. It is noted that while a single memory is described, a wide variety of types and combinations of memory (e.g., tangible, non-transitory memory) can be employed. The memory can be integral with the processor, can comprise stand-alone memory, or can be a combination of both. The memory can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 1000 and/or the memory can include removable integrated circuit card (ICC) memory, such as memory provided by a subscriber identity module (SIM) card, a universal subscriber identity module (USIM) card, a universal integrated circuit card (UICC), and so on.

The system 1000 includes a communications interface. The communications interface is operatively configured to communicate with components of the system 1000. For example, the communications interface can be configured to transmit data for storage in the system 1000, retrieve data from storage in the system 1000, and so forth. The communications interface is also communicatively coupled with the processor to facilitate data transfer between components of the system 1000 and the processor (e.g., for communicating inputs to the processor received from a device communicatively coupled with the system 1000 and/or communicating output to a device communicatively coupled with the system 1000. It is noted that while the communications interface is described as a component of a system 1000, one or more components of the communications interface can be implemented as external components communicatively coupled to the system 1000 via a wired and/or wireless connection. The system 1000 can also comprise and/or connect to one or more input/output (I/O) devices (e.g., via the communications interface) including, but not necessarily limited to: a display, a mouse, and so on.

The communications interface and/or the processor can be configured to communicate with a variety of different networks including, but not necessarily limited to: a wide-area cellular telephone network, such as a 3G cellular network, a 4G cellular network, or a global system for mobile communications (GSM) network; a wireless computer communications network, such as a WiFi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface can be configured to communicate with a single network or multiple networks across different access points.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A sample identification system for an automated sampling and dispensing device comprising:
    a sample probe configured to contact a sample positioned within a sample vessel, the sample having a corresponding sample identifier positioned proximate the sample vessel;
    an identifier capture device configured to detect the sample identifier positioned proximate the sample vessel and generate a data signal in response thereto, the data signal corresponding to an identity of the sample;
    a surface structure positioned between the sample probe and the identifier capture device, the surface structure configured to support the sample vessel relative to the sample probe, the surface structure positioned proximate a gap through which the identifier capture device is configured to move, aligned with the sample probe, to detect the sample identifier; and
    a sample arm assembly comprising a sample probe support arm and configured to support the sample probe, the sample arm assembly operable to translationally and rotationally align the sample probe to contact the sample positioned within the sample vessel.

2. The sample identification system as recited in claim 1, wherein the sample identifier includes a barcode.

3. The sample identification system as recited in claim 2, wherein the barcode includes a data matrix two-dimensional barcode.

4. The sample identification system as recited in claim 2, wherein the identifier capture device includes a barcode reader.

5. The sample identification system as recited in claim 1, wherein the data signal further corresponds to at least one of a location of the sample, a timestamp associated with when the automated sampling and dispensing device processed the sample, a presence of the sample, an absence of the sample, a type of analysis to be performed on the sample, or an extent of analysis to be performed on the sample.

6. The sample identification system as recited in claim 1, wherein the identifier capture device includes a fiber optic communication link.

7. The sample identification system as recited in claim 1, wherein the identifier capture device is communicatively coupled to at least one of a laboratory information management system or a laboratory instrument configured for identity verification of the sample.

8. A sample identification system for an automated sampling and dispensing device comprising:
- a sample probe configured to contact a sample positioned within a sample vessel, the sample having a corresponding sample identifier positioned proximate the sample vessel;
- an identifier capture device configured to detect the sample identifier positioned proximate the sample vessel, the identifier capture device including:
  - an alignment light source configured to provide an indication of alignment of the sample probe with the identifier capture device; and
  - an imaging device configured to generate a data signal responsive to detection of the sample identifier;
- a surface structure positioned between the sample probe and the identifier capture device, the surface structure configured to support the sample vessel relative to the sample probe, the surface structure positioned proximate a gap through which the identifier capture device is configured to move, aligned with the sample probe, to detect the sample identifier; and
- a sample arm assembly comprising a sample probe support arm and configured to support the sample probe, the sample arm assembly operable to translationally and rotationally align the sample probe to contact the sample positioned within the sample vessel.

9. The sample identification system as recited in claim 8, wherein the sample identifier comprises a barcode.

10. The sample identification system as recited in claim 9, wherein the barcode includes a data matrix two-dimensional barcode.

11. The sample identification system as recited in claim 9, wherein the identifier capture device includes a barcode reader.

12. The sample identification system as recited in claim 8, wherein the sample identifier uniquely corresponds to additional stored data.

13. The sample identification system as recited in claim 12, wherein the additional stored data includes at least one of a location of the sample, a type of analysis to be performed on the sample, an extent of analysis to be performed on the sample, a sample vial identification number, a destination vial identification number, a dilution factor (DF), a final volume, a sample volume, a diluent volume, and a diluent location.

14. The sample identification system as recited in claim 8, wherein the sample identifier is positioned on a bottom surface of the sample vessel.

15. The sample identification system as recited in claim 8, wherein the identifier capture device is communicatively coupled to at least one of a laboratory information management system or a laboratory instrument configured for identity verification of the sample.

16. The sample identification system as recited in claim 8, wherein the identifier capture device further includes a light source oriented to illuminate the sample identifier.

17. The sample identification system as recited in claim 8, further including:
- a sample holder configured to support the sample vessel, the sample holder defining at least one aperture through which the sample vessel passes for support.

18. The sample identification system as recited in claim 17, wherein the sample holder further includes a bottom portion comprising a light transmissive material.

19. The sample identification system as recited in claim 17, wherein the sample holder includes at least one aperture having a smaller cross-sectional area than a portion of the sample vessel.

20. The sample identification system as recited in claim 8, defining a gap beneath a surface supporting the sample vessels through which the identifier capture device is configured to move to detect the sample identifier.

* * * * *